(12) United States Patent
Rapsch et al.

(10) Patent No.: US 10,556,926 B2
(45) Date of Patent: Feb. 11, 2020

(54) SYNTHETIC ARTIFICIAL PEPTIDES WITH ANTIMICROBIAL EFFECT

(71) Applicant: FRAUNHOFER-GESELLSCHAFT ZUR FÖRDERUNG DER ANGEWANDTEN FORSCHUNG E.V., Munich (DE)

(72) Inventors: Karsten Rapsch, Berlin (DE); Markus v. Nickisch-Rosenegk, Grossbeeren (DE)

(73) Assignee: Fraunhofer-Gesellschaft, Munich (DE)

( * ) Notice: Subject to any disclaimer, the term of this patent is extended or adjusted under 35 U.S.C. 154(b) by 0 days.

(21) Appl. No.: 14/616,981

(22) Filed: Feb. 9, 2015

(65) Prior Publication Data

US 2015/0225458 A1   Aug. 13, 2015

(30) Foreign Application Priority Data

Feb. 11, 2014   (DE) .................. 10 2014 101 663

(51) Int. Cl.
| | | |
|---|---|---|
| *C07K 7/08* | (2006.01) | |
| *C07K 7/06* | (2006.01) | |
| *A61K 38/08* | (2019.01) | |
| *A61K 38/10* | (2006.01) | |
| *A61K 38/00* | (2006.01) | |

(52) U.S. Cl.
CPC ............... *C07K 7/08* (2013.01); *A61K 38/08* (2013.01); *A61K 38/10* (2013.01); *C07K 7/06* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,110,833 A | 5/1992 | Mosbach | |
| 5,958,786 A | 9/1999 | Munkholm | |
| 2003/0070548 A1 | 4/2003 | Clausen | |
| 2003/0166798 A1 | 9/2003 | Sellergren et al. | |
| 2005/0159570 A1 | 7/2005 | Sellergren et al. | |
| 2007/0106041 A1 | 5/2007 | Sellergren et al. | |
| 2008/0038832 A1 | 2/2008 | Sellergren et al. | |
| 2008/0131451 A1* | 6/2008 | Tanzi ................. | A61K 39/21 424/188.1 |
| 2009/0045056 A1 | 2/2009 | Berberich et al. | |
| 2009/0105449 A1* | 4/2009 | Tomich ............... | C07K 14/705 530/330 |

FOREIGN PATENT DOCUMENTS

| | | | |
|---|---|---|---|
| DE | 102004049805 A1 | 4/2006 | |
| DE | 112011100556 | 3/2013 | |
| EP | 2168590 A1 | 3/2010 | |
| EP | 1 757 943 | * | 10/2010 |
| JP | 2006067968 | * | 1/2006 |
| WO | 01/55095 A1 | | 8/2001 |
| WO | WO2003/092736 | * | 11/2003 |
| WO | WO2006-050611 | * | 5/2006 |
| WO | WO 2008/022444 | * | 2/2008 |
| WO | 2009064245 A1 | | 5/2009 |
| WO | WO 2011/121289 | * | 10/2011 |
| WO | 20121145680 A2 | | 10/2012 |

OTHER PUBLICATIONS

Takeuchi et al. ("B-Z transition of poly(dG-mdC) induced by binding of Lys-containing peptide" FEBS vol. 279 (2), 253-255, 1991).*
Maeda et al. ("Helix stabilizing effects of pentapeptide JIFMK and its related peptides on the sodium channel inactivation gate peptide" J. Peptide Research, 2001,58,413-423).*
Moreno et al. (The FEBS Journal; 272 (2005) 341-352).*
MedicineNet.com (accessed Sep. 13, 2017.*
Biologyonline.com (accessed Sep. 13, 2017).*
UniProt KB G0R1A9_ICHMG[online]. [retrieved online Jan. 6, 2018]. Retrieved from the internet: < http://www.uniprot.org/uniprot/G0R1A9> available 2011.*
Hilpert et al. ("Screening and Characterization of Suface-Tethered Cationic Peptides for Antimicrobial Activity" Chemistry & Biology 16,58-59; 2009).*
Papo et al. ("The consequence of sequence alteration of an amphipathic α-helical antimicrobial peptide and its diasteromers" The Journal of Biological Chemistry; vol. 277 (37) (2002) pp. 33913-33291).*
LifeTein (https://www.lifetein.com/Peptide-Synthesis-Amidation-Acetylation.html May 10, 2012).*
Schwartz et al. (BioPolymers vol. 15; 1377-1395, 1976).*
Langosch et al. (J. Mol. Biol. (2001) 311, 709-721).*
"Determination of minimum inhibitory concentrations (MICs) of antibacterial agents by broth dilution" Clinical Microbiology and Infection, vol. 9, No. 8, Aug. 2003, European Committee for Antimicrobial Susceptability Testing (EUCAST) of the European Society of Clinical Microbiology and Infectious Diseases (ESCMID).
Ahmad, A. et al.: "Design of Nontoxic Analogues of Cathelicidin-Derived Bovine Antimicrobial Peptide BMAP-27: The Role of Leucine as Well as Phenylalanine Zipper Sequences in Determining Its Toxicity" Biochemistry, vol. 48, No. 46, 2009, pp. 10905-10917.
Bell, G. et al.: "Arming the enemy: the ev olution of resistance to self-proteins" Microbiology vol. 149, 2003, pp. 1367-137.
Brogden, K. A. et al.: "Antimicrobial peptides in animals and their role in host defenses" Elsevier, International Journal of Antimicrobial Agents vol. 22, 2003, pp. 465-478.
Brogden, K. A. et al.: "Antimicrobial peptides: pore formers or metabolic inhibitors in bacteria?" Nature Reviews Microbiology vol. 3, Mar. 2003, pp. 238-250.

(Continued)

*Primary Examiner* — James H Alstrum-Acevedo
*Assistant Examiner* — Tara L Martinez
(74) *Attorney, Agent, or Firm* — Harness, Dickey & Pierce, P.L.C.

(57) ABSTRACT

The present invention relates to antimicrobial peptides of the general formula $A_xB_yC_z$ with x, z≥1, y≥3 and x+y+z≤50, where A and C, in each case independently of one another, have at least 65% basic amino acids and B has at least 65% hydrophobic and/or nonpolar amino acids and comprises a direct sequence of at least three hydrophobic amino acids. Moreover, a medical use of the peptides, a conjugate and an antimicrobial composition are indicated.

10 Claims, 6 Drawing Sheets
Specification includes a Sequence Listing.

(56) References Cited

OTHER PUBLICATIONS

Brötz, H. et al.: "The Lantibiotic Mersacidin Inhibits Peptidoglycan Synthesis by Targeting Lipid II" Antimicrobial Agents and Chemotherapy vol. 42, No. 1, 1998, pp. 154-160.
Conlon, J. M. et al.: "A melittin-related peptide from the skin of the Japanese frog, Rana tagoi, with antimicrobial and cytolytic properties" Biochemical and Biophysical Research Communications, vol. 306, 2003, pp. 496-500.
Dathe, M. et al.: "Hydrophobicity, hydrophobic moment and angle subtended by charged residues modulate antibacterial and haemolytic activity of amphipathic helical peptides" FEBS Letters, vol. 403, 1997, pp. 208-212.
Diamond, G.: "Nature's antibiotics: the potential of antimicrobial peptides as new drugs" Biologist, vol. 48, No. 5, 2001, pp. 209-212.
Gautier, R. et al.: "HELIQUEST: a web server to screen sequences with specific alpha-helical properties" Bioinformatics Applications Note, vol. 24, No. 18, 2008, pp. 2101-2102.
Gennaro, R. et al.: "Structural Features and Biological Activities of the Cathelicidin-Derived Antimicrobial Peptides" Biopolymers (Peptide Science), vol. 55, 2000, pp. 31-49.
Ginsburg, I. et al.: "Are cationic antimicrobial peptides also 'double-edged swords'?" Expert Reviews Anti Infect. Ther. vol. 6, No. 4, 2008, pp. 453-462.
Giuliani, A. et al.: "Antimicrobial peptides: an ov erv iew of a promising class of therapeutics. Central European" Central European Journal of Biology, vol. 2, No. 1, 2007, pp. 1-33.
Gordon Y. F. et al.: A Review of Antimicrobial Peptides and Their Therapeutic Potential as Anti-Infective Drugs Curr. Eye. Res. vol. 30, No. 7 2005, pp. 505-515.
Hilpert, K. et al.: "Short Cationic Antimicrobial Peptides Interact with ATP" American Society for Microbiology, Antimicrobial Agents Chemotherapy, vol. 54, No. 10, 2010, pp. 4480-4483.
Jin, Y. et al.: "Antimicrobial Activities and Structures of Two Linear Cationic Peptide Families with Various Amphipathic beta-Sheet and alpha-Helical Potentials" American Society for Microbiology, Antimicrobial Agents Chemotherapy, vol. 49, No. 12, 2005, pp. 4957-4964.
Kaur, H. et al.: "PEPstr: A de novo Method for Tertiary Structure Prediction of Small Bioactive Peptides" Bentham Science Publisher Ltd., Protein & Peptide Letters, vol. 14, 2007, pp. 626-631.
Lehrer, R. I. et al.: "Defensins of vertebrate animals" Elsevier Science, Current Opinion in Immunology, vol. 14, 2002, pp. 96-102.
Marr, A. K. et al.: "Antibacterial peptides for therapeutic use: obstacles and realistic outlook" Elsevier, Current Opinion in Pharmacology, vol. 6, 2006, pp. 468-472.
Maupetit, J. et al.: "A Fast Method for Large-Scale De Novo Peptide and Miniprotein Structure Prediction" Wiley Periodicals, Inc., J. Comput. Chem., vol. 31, 2010, pp. 726-738.
Maupetit, J. et al.: "PEP-FOLD: an online resource for de nov o peptide structure prediction" Nucleic. Acids. Res. 37, 2009, pp. W498-W503.
Ong, Z. Y. et al.: "Short Synthetic β-Sheet Forming Peptide Amphiphiles as Broad Spectrum Antimicrobials with Antibiofilm and Endotoxin Neutralizing Capabilities" Advanced Functional Materials, vol. 23, 2013, pp. 3682-3692.
Otvos, L. et al.: "Interaction between heat shock proteins and antimicrobial peptides" Biochemistry, vol. 39, 2000, pp. 14150-14159.
Oyston, P. C. et al.: "Novel peptide therapeutics for treatment of infections." Journal of Medical Microbiology, vol. 58, 2009, pp. 977-987.
Pettersen, E. F. et al.: "UCSF Chimera—A Visualization System for Exploratory Research and Analysis" Wiley Periodicals Inc., Journal of Computational Chemistry, vol. 25, 2004, pp. 1605-1612.
Rausch, J. M. et al.: "Beta-Sheet Pore-Forming Peptides Selected from a Rational Combinatorial Library: Mechanism of Pore Formation in Lipid Vesicles and Activity in Biological Membranes" Biochemistry, vol. 46, No. 43, 2007, 12124-12139.
Rausch, J. M. et al.: "Rational combinatorial design of pore-forming beta-sheet peptides" The National Academy of Sciences of the USA, vol. 102, No. 30, 2005, pp. 10511-10515.
Shai, Y.: "Mechanism of the binding, insertion and destabilization of phospholipid bilayer membranes by alpha-helical antimicrobial and cell non-selectiv e membrane-lytic peptides." Elsevier Science B.V., Biochimica Biophysica Acta, 1462, 1999, pp. 55-70.
Subbalakshmi, C. et al.: "Mechanism of antimicrobial action of indolicidin" Elsevier, FEMS Microbiology Letters 160, 1998, pp. 91-96.
Thévenet, P. et al.: "PEP-FOLD: an updated de nov o structure prediction server for both linear and disulfide bonded cyclic peptides" Nucleic. Acids. Res., vol. 40, 2012, Web Server issu, pp. W288-W293.
Tossi, A. et al.: "Amphipathic, alpha-Helical Antimicrobial Peptides." Biopolymers 55, 2000, pp. 4-30.
Wiegand, I. et al.: "Agar and broth dilution methods to determine the minimal inhibitory concentration (MIC) of antimicrobial substances" Centre for Microbial Diseases and Immunity Research, Nature Protocols, vol. 3, No. 2, 2008, pp. 163-17.
Wiradharma, N. et al.: "Rationally Designed alpha-Helical Broad-Spectrum Antimicrobial Peptides with Idealized Facial Amphiphilicity" Macromolecular Rapid Communications, vol. 34, 2013, pp. 74-80.
Zaiou, M.: "Multifunctional antimicrobial peptides: therapeutic targets in several human diseases" Springer-Verlag, J. Mol. Med. (Berl) 85, 2007, pp. 317-329.
Pag, et al., "In Vitro Activity and Mode of Action of Diastereomeric Antimicrobial Peptides Against Bacterial Clinical Isolates", Journal of Antimicrobial Chemotherapy, vol. 53, No. 2, 2004, pp. 230-239.
Rapsch, et al., "Rational Design of Artificial [beta]-Strand-Forming Antimicrobial Peptides with Biocompatible Properties", Molecular Pharmaceutics, vol. 11, No. 10, 2014, pp. 3492-3502.
Maeda, et al., "Helix-Stabilizing Effects of the Pentapeptide KIFMK and its Related Peptides on the Sodium Channel Inactivation Gate Peptides", Journal of Peptide Research, vol. 58, No. 5, 2001, pp. 413-423.
International Search Report for PCT/EP2013/072903, ISA/EP, Rijswijk, NL, dated Feb. 14, 2013 (3 pages).
Athikomrattanakul et al "Preparation and characterization of novel molecularly imprinted polymers based on thiourea receptors for nitrocompounds recognition" Elsevier, Talanta, vol. 84, No. 2 (2011) pp. 274-279.
Athikomrattanakul et al. "Prepareation of Molecularly Imprinted Polymers based on a New Tailor-Made Functional Monomer for Creatinine Binding" Poster (P3 59), May 17, 2012, Biosensors 2012, Cancun, Mexico.
Athikomrattanakul et al "Synthetic receptors for neutral nitro derivatives" Elsevier, Tetrahedron Letters, vol. 50 (2009) pp. 359-362.
Athikomrattanakul et al. "Thermometric Sensing of Nitrofurantoin by Noncovalently Imprinted Polymers Containing Two Complementary Functional Monomers" Analytical Chemistry, vol. 83, No. 20 (2011) pp. 7704-7711.
Benkert et al. "Development of a Creatinine ELISA and an Amperometric Antibody-Based Creatinine Sensor with a Detection Limit in the Nanomolar Range" Analytical Chemistry, vol. 72 (2000) pp. 916-921.
Chang et al. "Synthesis of an Imprinted Hybrid Organic-Inorganic Polymeric Sol-Gel Matrix Toward the Specific Binding and Isotherm Kinetics Investigation of Creatinine" Analytical Chemistry, vol. 81 (2009) pp. 2098-2105.
Fossati et al. "Enzymic Creatinine Assay: A New Colorimetric Method Based on Hydrogen Peroxide Measurement" Clinical Chemistry, vol. 29 (1983) pp. 1494-1496.
Gao et al. "Preparation and recognition performance of creatinine-imprinted material prepared with novel surface-imprinting technique" Elsevier, Journal of Chromatography, vol. 878 (2010) pp. 2077-2086.
Grabowska et al. "Determination of creatinine in clinical samples based on flow-through microsystem" Elsevier, Analytica Chimica Acta, vol. 540 (2005) pp. 181-185.

(56) References Cited

OTHER PUBLICATIONS

Hsieh et al. "Designing a molecularly imprinted polymer as an artificial receptor for the specific recognition of creatinine in serums" elsevier, Biomaterials, vol. 27 (2006) pp. 2083-2089.

Huang et al. "Urinalysis with molecularly imprinted poly(ethylene-co-vinyl alcohol) potentiostat sensors" Elsevier, Biosensors and Bioelectronics, vol. 24, No. 8 (2009) pp. 2611-2617.

Jaffe "A New Reaction for Assessing Creatinine" Strassburg Verlag, Zeitschrift für Physiologische Chemie 10 (1886) pp. 391-400 with English Abstract.

Jiugao et al. "The preparation of cellulose nitrate derivatives and their adsorption properties for creatinine" Elsevier, Carbohydrate Polymers, vol. 70 (2007) pp. 8-14.

Khadro et al. "Molecularly imprinted polymers (MIP) based electrochemical sensor for detection of urea and creatinine" Elsevier, Procedia Engineering, vol. 5 (2010) pp. 371-374.

Kubo et al. "Immobilization of Creatinine Deiminase on a Substituted Poly(methyglutamate) Membrane and its use in a Creatinine Sensor" Elsevier, Analytics Chimica Acta, 187 (1986) pp. 31-37.

Lakshmi et al. "Creatinine sensor based on a molecularly imprinted polymer-modified hanging mercury drop electrode" Elsevier, Talanta, vol. 70 (2006) pp. 272-280.

Lee et al. "Recognition of creatinine by poly(ethylene-co-vinyl-alcohol) molecular imprinting membrane" Elsevier, Desalination, vol. 234 (2008) pp. 126-133.

Lee et al. "Synthesis of Magnetic Molecularly Imprinted Poly(ethylene-co-vinyl alcohol) Nanoparticles and Their Uses in the Extraction and Sensing of Target Molecules in Urine" ACS Applied Materials & Interfaces, vol. 2 (2010) pp. 1729-1736.

Lettau et al. "A Bifunctional Molecularly Imprinted Polymer (MIP): Analysis of Binding and Catalysis by a Thermistor" Wiley-VCH Verlag, Angewan. Chem. Int. Ed., 45 (2006), pp. 6986-6990.

Lettau et al. "Sequential conversion by catalytically active MIP and immobilized tyrosinase in a thermistor" Elsevier, Biosensors & Bioelectronics, vol. 23 (2008), pp. 1216-1219.

Li et al. "Preparation of a novel molecularly imprinted polymer by the sol-gel process for sensing creatinine" Elsevier, Analytica Chimica Acta, vol. 711 (2012) pp. 83-90.

Lin et al. "Instant formation of molecularly imprinted poly(ethylene-co-vinyl alcohol)/quantum dot composite nanoparticles and their use in one-pot urinalysis" Elsevier, Biosensors and Bioelectronics, vol. 25 (2009) pp. 579-586.

Panasyuk-Delaney et al. "Capacitive Creatinine Sensor Based on a Photografted Molecularly Imprinted Polymer" Wiley-VCH Verlag, Electroanalysis, vol. 14, No. 3 (2002) pp. 221-224.

Patel et al. "Development of a Creatinine Sensor Based on a Molecularly Imprinted Polymer-Modified Sol-Gel Film on graphite Electrode" Wiley-VCH Verlag, Electroanalysis, vol. 20 (2008) pp. 2102-2112.

Rajkumar et al. "Thermometric MIP sensor for fructosyl valine" Elsevier, Biosensors & Bioelectronics, vol. 23 (2008) pp. 1195-1199.

Ramanathan et al. "Principles and application of thermal biosensors" Elsevier, Biosensors & Bioelectronics, vol. 16 (2001), pp. 417-423.

Reddy et al. "Artificial Biomolecular Recognition Element Based Sensor for Electrochemical Impedance Detection of Creatinine" International Conference on Nanotechnology and Biosensors IPCBEE, vol. 25 (2011) pp. 25-29.

Sharma et al. "Highly Sensitive and Selective Detection of Creatinine by Combined Use of MISPE and a Complementary MIP-Sensor" GWV Fachverlage, Chromatographia, vol. 65 (2007) pp. 419-427.

Soldatkin et al. "Creatinine sensitive biosensor based on ISFETs and creatinine deiminase immobilised in BSA membrane" Elsevier, Talanta, vol. 58 (2002) pp. 351-357.

Sreevivasan et al. "Interaction of Molecularly Imprinted Polymers with Creatinine" Journal of Applied Polymer Science, vol. 66 (1997) pp. 2539-2542.

Stöcklein et al. "Enzyme kinetic assays with surface plamon resonance (BIAcore) based on competition between enzyme and creatinine antibody" Elsevier, Biosensors & Bioelectronics, vol. 15 (2000) pp. 377-382.

Subat et al. "Synthetic Creatinine Receptor: Imprinting of a Lewis Acidic Zind(II)cycelen Binding Site to Shape its Molelecular Recognition Selectivity" JACS Articles, American Chemical Society, vol. 126 (2004) 3185-3190.

Subrahmanyam et al. "'Bite-and-Switch' approach using computationally designed molecularly imprinted polymers for sensing of creatine" Elsevier, Biosensors & bioelectronics, vol. 16 (2001) pp. 631-637.

Syu et al. "Synthesis of Recognition Matrix from 4-Methylamino-N-Allylnaphthal-Imide with Fluorescent Effect for the Imprinting of Creatinine" American Chemical Society, Analytical Chemistry, vol. 82 (2010) pp. 8821-8829.

Tsai et al. "Preparation of imprinted poly(tetraethoxysilanol) sol-gel for the specific uptake of creatinine" Elsevier, Chemical Engineering Journal, vol. 168 (2011) pp. 1369-1376.

Tsai et al. "Synthesis and characterization of creatinine imprinted poly(4-vinylpyridine-co-divinylbenzene) as a specific recognition receptor" Elsevier, Analytica Chimica Acta, vol. 539 (2005) pp. 107-116.

Tsai et al. "Synthesis of Creatinine-imprinted poly(ß-cyclodextrin) for the specific binding of creatinine" Elsevier, Biomaterials, vol. 26 (2005) pp. 2759-2766.

Tsai et al. "Multiple type biosensors fabricated using the CMOS BioMEMS platform" Elsevier, Sensors and Actuators B: Chemical, vol. 144 (2010) pp. 407-412.

Walsh et al. "comparison of electrochemical, electrophoretic and spectrophotometric methods for creatinine determination in biological fluids" Elsevier, Analytica Chimica Acta, vol. 459 (2002) pp. 187-198.

Weber et al. "Interferences in Current Methods for Measurements of Creatinine" Clinical Chemistry, vol. 37, No. 5 (1991) pp. 695-700.

Yadav et al. "Amperometric creatinine biosensor based on covalently coimmobilized enzymes onto carboxylated multiwalled carbon nanotubes/polyaniline composite film" Elsevier, Analytica Biochemistry, vol. 419 (2011) pp. 277-283.

Bergmeyer, H.U. et al, "Lipids, Amino Acids and Related Compounds", Methods of Enzymatic Analysis VIII, 3rd edition (1985), pp. 448-507, vol. 8.

Skarzynski, Carol J. et al, "Renal Function", Clinical Chemistry, 4th edition, (2000), pp. 440-462, Lippincott Williams & Wilkins, US.

Pag, U. et al.: "In vitro activity and mode of action of diastereomeric antimicrobial peptides against bacterial clinical isolates", Journal of Antimicrobial Chemotherapy, vol. 53, No. 2, 2004 pp. 230-239.

Rapsch, I. et al.: "Rational Design of Artificial [beta]-Strand-Forming Antimicrobial Peptides with Biocompatible Properties", Molecular Pharmaceutics, vol. 11, No. 10, 2014, pp. 3492-3502.

Maeda, Y. et al.: "Helix-stabilizing effects of the pentapeptide KIFMK an its related peptides on the sodium channel inactivation gate peptides", Journal of Peptide Research, vol. 58, No. 5, 2001, pp. 413-423.

* cited by examiner

SEQUENCE LISTING

<160> NUMBER OF SEQ ID NOS: 79

<210> SEQ ID NO 1
<211> LENGTH: 11
<212> TYPE: PRT
<213> ORGANISM: Artificial
<220> FEATURE:
<223> OTHER INFORMATION: Synthetic peptide M1

<400> SEQUENCE: 1

Lys Arg Lys Ile Leu Ile Leu Ile Lys Arg Lys
1               5                   10

<210> SEQ ID NO 2
<211> LENGTH: 13
<212> TYPE: PRT
<213> ORGANISM: Artificial
<220> FEATURE:
<223> OTHER INFORMATION: Synthetic peptide N1

<400> SEQUENCE: 2

Lys Arg Lys Arg Lys Ile Leu Ile Leu Ile Lys Arg Lys
1               5                   10

<210> SEQ ID NO 3
<211> LENGTH: 12
<212> TYPE: PRT
<213> ORGANISM: Artificial
<220> FEATURE:
<223> OTHER INFORMATION: Synthetic Peptide N2

<400> SEQUENCE: 3

Arg Lys Arg Lys Ile Leu Ile Leu Ile Lys Arg Lys
1               5                   10

<210> SEQ ID NO 4
<211> LENGTH: 10
<212> TYPE: PRT
<213> ORGANISM: Artificial
<220> FEATURE:
<223> OTHER INFORMATION: Synthetic Peptide N3

<400> SEQUENCE: 4

Arg Lys Ile Leu Ile Leu Ile Lys Arg Lys
1               5                   10

<210> SEQ ID NO 5
<211> LENGTH: 9
<212> TYPE: PRT
<213> ORGANISM: Artificial
<220> FEATURE:
<223> OTHER INFORMATION: Synthetic peptide N4

<400> SEQUENCE: 5

Lys Ile Leu Ile Leu Ile Lys Arg Lys
1               5

<210> SEQ ID NO 6
<211> LENGTH: 13
<212> TYPE: PRT
<213> ORGANISM: Artificial
<220> FEATURE:
<223> OTHER INFORMATION: Synthetic peptide C1

<400> SEQUENCE: 6

Lys Arg Lys Ile Leu Ile Leu Ile Lys Arg Lys Arg Lys
1               5                   10

```
<210> SEQ ID NO 7
<211> LENGTH: 12
<212> TYPE: PRT
<213> ORGANISM: Artificial
<220> FEATURE:
<223> OTHER INFORMATION: Synthetic peptide C2

<400> SEQUENCE: 7

Lys Arg Lys Ile Leu Ile Leu Ile Lys Arg Lys Arg
1               5                   10

<210> SEQ ID NO 8
<211> LENGTH: 10
<212> TYPE: PRT
<213> ORGANISM: Artificial
<220> FEATURE:
<223> OTHER INFORMATION: Synthetic peptide C3

<400> SEQUENCE: 8

Lys Arg Lys Ile Leu Ile Leu Ile Lys Arg
1               5                   10

<210> SEQ ID NO 9
<211> LENGTH: 9
<212> TYPE: PRT
<213> ORGANISM: Artificial
<220> FEATURE:
<223> OTHER INFORMATION: Synthetic peptide C4

<400> SEQUENCE: 9

Lys Arg Lys Ile Leu Ile Leu Ile Lys
1               5

<210> SEQ ID NO 10
<211> LENGTH: 13
<212> TYPE: PRT
<213> ORGANISM: Artificial
<220> FEATURE:
<223> OTHER INFORMATION: Synthetic peptide H1

<400> SEQUENCE: 10

Lys Arg Lys Ile Leu Ile Leu Ile Leu Ile Lys Arg Lys
1               5                   10

<210> SEQ ID NO 11
<211> LENGTH: 10
<212> TYPE: PRT
<213> ORGANISM: Artificial
<220> FEATURE:
<223> OTHER INFORMATION: Synthetic peptide H2

<400> SEQUENCE: 11

Lys Arg Lys Leu Ile Leu Ile Lys Arg Lys
1               5                   10

<210> SEQ ID NO 12
<211> LENGTH: 9
<212> TYPE: PRT
<213> ORGANISM: Artificial
<220> FEATURE:
<223> OTHER INFORMATION: Synthetic peptide H3

<400> SEQUENCE: 12

Lys Arg Lys Ile Leu Ile Lys Arg Lys
1               5
```

```
<210> SEQ ID NO 13
<211> LENGTH: 14
<212> TYPE: PRT
<213> ORGANISM: Artificial
<220> FEATURE:
<223> OTHER INFORMATION: Synthetic peptide A1

<400> SEQUENCE: 13

Arg Lys Arg Lys Leu Ile Leu Ile Leu Ile Lys Arg Lys Arg
1               5                   10

<210> SEQ ID NO 14
<211> LENGTH: 14
<212> TYPE: PRT
<213> ORGANISM: Artificial
<220> FEATURE:
<223> OTHER INFORMATION: Synthetic peptide A2

<400> SEQUENCE: 14

Lys Arg Lys Leu Ile Leu Lys Arg Ile Leu Ile Lys Arg Lys
1               5                   10

<210> SEQ ID NO 15
<211> LENGTH: 11
<212> TYPE: PRT
<213> ORGANISM: Artificial
<220> FEATURE:
<223> OTHER INFORMATION: Synthetic peptide S1

<400> SEQUENCE: 15

Arg Arg Arg Ile Ile Ile Ile Ile Arg Arg Arg
1               5                   10

<210> SEQ ID NO 16
<211> LENGTH: 11
<212> TYPE: PRT
<213> ORGANISM: Artificial
<220> FEATURE:
<223> OTHER INFORMATION: Synthetic peptide S2

<400> SEQUENCE: 16

Lys Lys Lys Ile Ile Ile Ile Ile Lys Lys Lys
1               5                   10

<210> SEQ ID NO 17
<211> LENGTH: 11
<212> TYPE: PRT
<213> ORGANISM: Artificial
<220> FEATURE:
<223> OTHER INFORMATION: Synthetic peptide S3

<400> SEQUENCE: 17

Arg Arg Arg Leu Leu Leu Leu Leu Arg Arg Arg
1               5                   10

<210> SEQ ID NO 18
<211> LENGTH: 11
<212> TYPE: PRT
<213> ORGANISM: Artificial
<220> FEATURE:
<223> OTHER INFORMATION: Synthetic peptide S4

<400> SEQUENCE: 18

Lys Lys Lys Leu Leu Leu Leu Leu Lys Lys Lys
1               5                   10
```

```
<210> SEQ ID NO 19
<211> LENGTH: 11
<212> TYPE: PRT
<213> ORGANISM: Artificial
<220> FEATURE:
<223> OTHER INFORMATION: Synthetic peptide S5

<400> SEQUENCE: 19

Arg Arg Arg Val Val Val Val Val Arg Arg Arg
1               5                   10

<210> SEQ ID NO 20
<211> LENGTH: 11
<212> TYPE: PRT
<213> ORGANISM: Artificial
<220> FEATURE:
<223> OTHER INFORMATION: Synthetic peptide S6

<400> SEQUENCE: 20

Lys Lys Lys Val Val Val Val Val Lys Lys Lys
1               5                   10

<210> SEQ ID NO 21
<211> LENGTH: 11
<212> TYPE: PRT
<213> ORGANISM: Artificial
<220> FEATURE:
<223> OTHER INFORMATION: Synthetic peptide S7

<400> SEQUENCE: 21

Arg Arg Arg Phe Phe Phe Phe Phe Arg Arg Arg
1               5                   10

<210> SEQ ID NO 22
<211> LENGTH: 11
<212> TYPE: PRT
<213> ORGANISM: Artificial
<220> FEATURE:
<223> OTHER INFORMATION: Synthetic peptide S8

<400> SEQUENCE: 22

Lys Lys Lys Phe Phe Phe Phe Phe Lys Lys Lys
1               5                   10

<210> SEQ ID NO 23
<211> LENGTH: 15
<212> TYPE: PRT
<213> ORGANISM: Artificial
<220> FEATURE:
<223> OTHER INFORMATION: Synthetic peptide D4

<400> SEQUENCE: 23

Lys Lys Lys Lys Lys Ile Ile Ile Ile Ile Lys Lys Lys Lys Asp
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthetic peptide D5

<400> SEQUENCE: 24

Lys Lys Lys Lys Lys Ile Ile Ile Ile Ile Lys Lys Lys Lys Lys
1               5                   10                  15
```

```
<210> SEQ ID NO 25
<211> LENGTH: 15
<212> TYPE: PRT
<213> ORGANISM: Artificial
<220> FEATURE:
<223> OTHER INFORMATION: Synthetic peptide D6

<400> SEQUENCE: 25

Lys Lys Lys Lys Lys Ile Ile Ile Ile Ile Asp Lys Lys Lys Lys
1               5                   10                  15

<210> SEQ ID NO 26
<211> LENGTH: 15
<212> TYPE: PRT
<213> ORGANISM: Artificial
<220> FEATURE:
<223> OTHER INFORMATION: Synthetic peptide D7

<400> SEQUENCE: 26

Lys Lys Lys Lys Lys Ile Ile Ile Ile Ile Asp Asp Asp Lys Lys
1               5                   10                  15

<210> SEQ ID NO 27
<211> LENGTH: 12
<212> TYPE: PRT
<213> ORGANISM: Artificial
<220> FEATURE:
<223> OTHER INFORMATION: Synthetic peptide O1 and O1'

<400> SEQUENCE: 27

Lys Lys Lys Ile Ile Ile Ile Ile Ile Lys Lys Lys
1               5                   10

<210> SEQ ID NO 28
<211> LENGTH: 11
<212> TYPE: PRT
<213> ORGANISM: Artificial
<220> FEATURE:
<223> OTHER INFORMATION: Synthetic peptide Pe01

<400> SEQUENCE: 28

Lys Arg Lys Ile Leu Ile Leu Ile Lys Arg Lys
1               5                   10

<210> SEQ ID NO 29
<211> LENGTH: 11
<212> TYPE: PRT
<213> ORGANISM: Artificial
<220> FEATURE:
<223> OTHER INFORMATION: Synthetic peptide Pe02

<400> SEQUENCE: 29

Lys Arg Lys Phe Ile Phe Ile Phe Lys Arg Lys
1               5                   10

<210> SEQ ID NO 30
<211> LENGTH: 15
<212> TYPE: PRT
<213> ORGANISM: Artificial
<220> FEATURE:
<223> OTHER INFORMATION: Synthetic peptide Pe10

<400> SEQUENCE: 30

Lys Lys Lys Trp Lys Ile Val Val Ile Arg Lys Lys Lys Arg Lys
1               5                   10                  15
```

```
<210> SEQ ID NO 31
<211> LENGTH: 7
<212> TYPE: PRT
<213> ORGANISM: Artificial
<220> FEATURE:
<223> OTHER INFORMATION: Synthetic peptide Z1

<400> SEQUENCE: 31

Arg Lys Leu Ile Leu Lys Arg
1               5

<210> SEQ ID NO 32
<211> LENGTH: 14
<212> TYPE: PRT
<213> ORGANISM: Artificial
<220> FEATURE:
<223> OTHER INFORMATION: Synthetic peptide Z2

<400> SEQUENCE: 32

Lys Lys Lys Lys Lys Ile Ile Ile Lys Lys Lys Lys Lys Lys
1               5                   10

<210> SEQ ID NO 33
<211> LENGTH: 15
<212> TYPE: PRT
<213> ORGANISM: Artificial
<220> FEATURE:
<223> OTHER INFORMATION: Synthetic peptide Z3

<400> SEQUENCE: 33

Lys Lys Lys Lys Lys Ile Ile Ile Ile Lys Lys Lys Lys Lys Lys
1               5                   10                  15

<210> SEQ ID NO 34
<211> LENGTH: 8
<212> TYPE: PRT
<213> ORGANISM: Artificial
<220> FEATURE:
<223> OTHER INFORMATION: Synthetic peptide Z4

<400> SEQUENCE: 34

Lys Lys Ile Ile Ile Ile Lys Lys
1               5

<210> SEQ ID NO 35
<211> LENGTH: 10
<212> TYPE: PRT
<213> ORGANISM: Artificial
<220> FEATURE:
<223> OTHER INFORMATION: Synthetic peptide Z5

<400> SEQUENCE: 35

Lys Lys Lys Ile Ile Ile Ile Lys Lys Lys
1               5                   10

<210> SEQ ID NO 36
<211> LENGTH: 12
<212> TYPE: PRT
<213> ORGANISM: Artificial
<220> FEATURE:
<223> OTHER INFORMATION: Synthetic peptide Z6

<400> SEQUENCE: 36

Lys Lys Lys Lys Ile Ile Ile Ile Lys Lys Lys Lys
1               5                   10
```

```
<210> SEQ ID NO 37
<211> LENGTH: 13
<212> TYPE: PRT
<213> ORGANISM: Artificial
<220> FEATURE:
<223> OTHER INFORMATION: Synthetic peptide Z7

<400> SEQUENCE: 37

Lys Lys Lys Ile Ile Ile Ile Ile Ile Ile Lys Lys Lys
1               5                   10

<210> SEQ ID NO 38
<211> LENGTH: 14
<212> TYPE: PRT
<213> ORGANISM: Artificial
<220> FEATURE:
<223> OTHER INFORMATION: Synthetic peptide Z8

<400> SEQUENCE: 38

Arg Arg Arg Arg Arg Ile Ile Ile Arg Arg Arg Arg Arg
1               5                   10

<210> SEQ ID NO 39
<211> LENGTH: 15
<212> TYPE: PRT
<213> ORGANISM: Artificial
<220> FEATURE:
<223> OTHER INFORMATION: Synthetic peptide Z9

<400> SEQUENCE: 39

Arg Arg Arg Arg Arg Ile Ile Ile Ile Arg Arg Arg Arg Arg
1               5                   10                  15

<210> SEQ ID NO 40
<211> LENGTH: 8
<212> TYPE: PRT
<213> ORGANISM: Artificial
<220> FEATURE:
<223> OTHER INFORMATION: Synthertic peptide Z10

<400> SEQUENCE: 40

Arg Arg Ile Ile Ile Ile Arg Arg
1               5

<210> SEQ ID NO 41
<211> LENGTH: 10
<212> TYPE: PRT
<213> ORGANISM: Artificial
<220> FEATURE:
<223> OTHER INFORMATION: Synthetic peptide Z11

<400> SEQUENCE: 41

Arg Arg Arg Ile Ile Ile Ile Arg Arg Arg
1               5                   10

<210> SEQ ID NO 42
<211> LENGTH: 12
<212> TYPE: PRT
<213> ORGANISM: Artificial
<220> FEATURE:
<223> OTHER INFORMATION: Synthetic peptide Z12

<400> SEQUENCE: 42

Arg Arg Arg Arg Ile Ile Ile Ile Arg Arg Arg Arg
1               5                   10
```

```
<210> SEQ ID NO 43
<211> LENGTH: 12
<212> TYPE: PRT
<213> ORGANISM: Artificial
<220> FEATURE:
<223> OTHER INFORMATION: Synthetic peptide Z13

<400> SEQUENCE: 43

Arg Arg Arg Ile Ile Ile Ile Ile Ile Arg Arg Arg
1               5                   10

<210> SEQ ID NO 44
<211> LENGTH: 12
<212> TYPE: PRT
<213> ORGANISM: Artificial
<220> FEATURE:
<223> OTHER INFORMATION: Synthetic peptide Z14

<400> SEQUENCE: 44

Arg Ile Arg Ile Ile Ile Ile Ile Ile Arg Ile Arg
1               5                   10

<210> SEQ ID NO 45
<211> LENGTH: 9
<212> TYPE: PRT
<213> ORGANISM: Artificial
<220> FEATURE:
<223> OTHER INFORMATION: Synthetic peptide Z15

<400> SEQUENCE: 45

Lys Lys Lys Ile Ile Ile Lys Lys Lys
1               5

<210> SEQ ID NO 46
<211> LENGTH: 9
<212> TYPE: PRT
<213> ORGANISM: Artificial
<220> FEATURE:
<223> OTHER INFORMATION: Synthetic peptide Z16

<400> SEQUENCE: 46

Arg Arg Arg Ile Ile Ile Arg Arg Arg
1               5

<210> SEQ ID NO 47
<211> LENGTH: 15
<212> TYPE: PRT
<213> ORGANISM: Artificial
<220> FEATURE:
<223> OTHER INFORMATION: Synthetic peptide Z17

<400> SEQUENCE: 47

Lys Lys Lys Lys Lys Ile Val Val Ile Lys Lys Lys Lys Lys
1               5                   10                  15

<210> SEQ ID NO 48
<211> LENGTH: 11
<212> TYPE: PRT
<213> ORGANISM: Artificial
<220> FEATURE:
<223> OTHER INFORMATION: Synthetic peptide Z18

<400> SEQUENCE: 48

Lys Arg Lys Phe Ile Phe Ile Phe Lys Arg Lys
1               5                   10
```

```
<210> SEQ ID NO 49
<211> LENGTH: 13
<212> TYPE: PRT
<213> ORGANISM: Artificial
<220> FEATURE:
<223> OTHER INFORMATION: Synthetic peptide Z19

<400> SEQUENCE: 49

Arg Arg Arg Ile Ile Ile Ile Ile Ile Ile Arg Arg Arg
1               5                   10

<210> SEQ ID NO 50
<211> LENGTH: 26
<212> TYPE: PRT
<213> ORGANISM: Artificial
<220> FEATURE:
<223> OTHER INFORMATION: Melittin

<400> SEQUENCE: 50

Gly Ile Gly Ala Val Leu Lys Val Leu Thr Thr Gly Leu Pro Ala Leu
1               5                   10                  15

Ile Ser Trp Ile Lys Arg Lys Arg Gln Gln
                20                  25

<210> SEQ ID NO 51
<211> LENGTH: 27
<212> TYPE: PRT
<213> ORGANISM: Artificial
<220> FEATURE:
<223> OTHER INFORMATION: BMAP-27

<400> SEQUENCE: 51

Gly Arg Phe Lys Arg Phe Arg Lys Lys Phe Lys Lys Leu Phe Lys Lys
1               5                   10                  15

Leu Ser Pro Val Ile Pro Leu Leu His Leu Gly
                20                  25

<210> SEQ ID NO 52
<211> LENGTH: 32
<212> TYPE: PRT
<213> ORGANISM: Artificial
<220> FEATURE:
<223> OTHER INFORMATION: Protamine

<400> SEQUENCE: 52

Met Pro Arg Arg Arg Arg Ser Ser Ser Arg Pro Val Arg Arg Arg Arg
1               5                   10                  15

Arg Pro Arg Val Ser Arg Arg Arg Arg Arg Gly Gly Arg Arg Arg Arg
                20                  25                  30

<210> SEQ ID NO 53
<211> LENGTH: 13
<212> TYPE: PRT
<213> ORGANISM: Artificial
<220> FEATURE:
<223> OTHER INFORMATION: Indolicidine

<400> SEQUENCE: 53

Ile Leu Pro Trp Lys Trp Pro Trp Trp Pro Trp Arg Arg
1               5                   10

<210> SEQ ID NO 54
<211> LENGTH: 15
<212> TYPE: PRT
<213> ORGANISM: Artificial
```

```
<220> FEATURE:
<223> OTHER INFORMATION: KL-Helix

<400> SEQUENCE: 54

Leu Lys Leu Leu Lys Lys Leu Lys Lys Leu Leu Lys Leu Leu
1               5                   10                  15

<210> SEQ ID NO 55
<211> LENGTH: 11
<212> TYPE: PRT
<213> ORGANISM: Artificial
<220> FEATURE:
<223> OTHER INFORMATION: Synthetic peptide M2

<400> SEQUENCE: 55

Lys Arg Lys Ile Leu Ile Leu Ile Leu Ile Leu
1               5                   10

<210> SEQ ID NO 56
<211> LENGTH: 11
<212> TYPE: PRT
<213> ORGANISM: Artificial
<220> FEATURE:
<223> OTHER INFORMATION: Synthetic peptide M3

<400> SEQUENCE: 56

Ile Leu Ile Leu Ile Leu Ile Leu Lys Arg Lys
1               5                   10

<210> SEQ ID NO 57
<211> LENGTH: 11
<212> TYPE: PRT
<213> ORGANISM: Artificial
<220> FEATURE:
<223> OTHER INFORMATION: Synthetic peptide M4

<400> SEQUENCE: 57

Lys Arg Lys Ile Leu Ile Leu Ile Gly Ser Gly
1               5                   10

<210> SEQ ID NO 58
<211> LENGTH: 11
<212> TYPE: PRT
<213> ORGANISM: Artificial
<220> FEATURE:
<223> OTHER INFORMATION: Synthetic peptide M5

<400> SEQUENCE: 58

Gly Ser Gly Ile Leu Ile Leu Ile Lys Arg Lys
1               5                   10

<210> SEQ ID NO 59
<211> LENGTH: 11
<212> TYPE: PRT
<213> ORGANISM: Artificial
<220> FEATURE:
<223> OTHER INFORMATION: Synthetic peptide M6

<400> SEQUENCE: 59

Lys Arg Lys Ser Gly Ser Gly Ser Lys Arg Lys
1               5                   10

<210> SEQ ID NO 60
<211> LENGTH: 8
<212> TYPE: PRT
<213> ORGANISM: Artificial
```

```
<220> FEATURE:
<223> OTHER INFORMATION: Synthetic peptide N5

<400> SEQUENCE: 60

Ile Leu Ile Leu Ile Lys Arg Lys
1               5

<210> SEQ ID NO 61
<211> LENGTH: 7
<212> TYPE: PRT
<213> ORGANISM: Artificial
<220> FEATURE:
<223> OTHER INFORMATION: Synthetic peptide N6

<400> SEQUENCE: 61

Leu Ile Leu Ile Lys Arg Lys
1               5

<210> SEQ ID NO 62
<211> LENGTH: 6
<212> TYPE: PRT
<213> ORGANISM: Artificial
<220> FEATURE:
<223> OTHER INFORMATION: Synthetic peptide N7

<400> SEQUENCE: 62

Ile Leu Ile Lys Arg Lys
1               5

<210> SEQ ID NO 63
<211> LENGTH: 5
<212> TYPE: PRT
<213> ORGANISM: Artificial
<220> FEATURE:
<223> OTHER INFORMATION: Synthetic peptide N8

<400> SEQUENCE: 63

Leu Ile Lys Arg Lys
1               5

<210> SEQ ID NO 64
<211> LENGTH: 8
<212> TYPE: PRT
<213> ORGANISM: Artificial
<220> FEATURE:
<223> OTHER INFORMATION: Synthetic peptide C5

<400> SEQUENCE: 64

Lys Arg Lys Ile Leu Ile Leu Ile
1               5

<210> SEQ ID NO 65
<211> LENGTH: 7
<212> TYPE: PRT
<213> ORGANISM: Artificial
<220> FEATURE:
<223> OTHER INFORMATION: Synthetic peptide C6

<400> SEQUENCE: 65

Lys Arg Lys Ile Leu Ile Leu
1               5

<210> SEQ ID NO 66
<211> LENGTH: 6
<212> TYPE: PRT
<213> ORGANISM: Artificial
```

```
<220> FEATURE:
<223> OTHER INFORMATION: Synthetic peptide C7

<400> SEQUENCE: 66

Lys Arg Lys Ile Leu Ile
1               5

<210> SEQ ID NO 67
<211> LENGTH: 5
<212> TYPE: PRT
<213> ORGANISM: Artificial
<220> FEATURE:
<223> OTHER INFORMATION: Synthetic peptide C8

<400> SEQUENCE: 67

Lys Arg Lys Ile Leu
1               5

<210> SEQ ID NO 68
<211> LENGTH: 8
<212> TYPE: PRT
<213> ORGANISM: Artificial
<220> FEATURE:
<223> OTHER INFORMATION: Synthetic peptide H4

<400> SEQUENCE: 68

Lys Arg Lys Leu Ile Lys Arg Lys
1               5

<210> SEQ ID NO 69
<211> LENGTH: 7
<212> TYPE: PRT
<213> ORGANISM: Artificial
<220> FEATURE:
<223> OTHER INFORMATION: Synthetic peptide H5

<400> SEQUENCE: 69

Lys Arg Lys Ile Lys Arg Lys
1               5

<210> SEQ ID NO 70
<211> LENGTH: 6
<212> TYPE: PRT
<213> ORGANISM: Artificial
<220> FEATURE:
<223> OTHER INFORMATION: Synthetic peptide H6

<400> SEQUENCE: 70

Lys Arg Lys Lys Arg Lys
1               5

<210> SEQ ID NO 71
<211> LENGTH: 7
<212> TYPE: PRT
<213> ORGANISM: Artificial
<220> FEATURE:
<223> OTHER INFORMATION: Synthetic peptide H7

<400> SEQUENCE: 71

Lys Arg Lys Gly Lys Arg Lys
1               5

<210> SEQ ID NO 72
<211> LENGTH: 9
<212> TYPE: PRT
<213> ORGANISM: Artificial
```

```
<220> FEATURE:
<223> OTHER INFORMATION: Synthetic peptide H8

<400> SEQUENCE: 72

Lys Arg Lys Gly Ser Gly Lys Arg Lys
1               5

<210> SEQ ID NO 73
<211> LENGTH: 14
<212> TYPE: PRT
<213> ORGANISM: Artificial
<220> FEATURE:
<223> OTHER INFORMATION: Synthetic peptide A3

<400> SEQUENCE: 73

Arg Lys Leu Ile Leu Lys Arg Lys Arg Ile Leu Ile Lys Arg
1               5                   10

<210> SEQ ID NO 74
<211> LENGTH: 14
<212> TYPE: PRT
<213> ORGANISM: Artificial
<220> FEATURE:
<223> OTHER INFORMATION: Synthetic peptid A4

<400> SEQUENCE: 74

Lys Leu Ile Leu Lys Arg Lys Arg Lys Arg Ile Leu Ile Lys
1               5                   10

<210> SEQ ID NO 75
<211> LENGTH: 14
<212> TYPE: PRT
<213> ORGANISM: Artificial
<220> FEATURE:
<223> OTHER INFORMATION: Synthetic peptide A5

<400> SEQUENCE: 75

Leu Ile Leu Lys Arg Lys Arg Lys Arg Lys Arg Ile Leu Ile
1               5                   10

<210> SEQ ID NO 76
<211> LENGTH: 15
<212> TYPE: PRT
<213> ORGANISM: Artificial
<220> FEATURE:
<223> OTHER INFORMATION: Synthetic peptide D1

<400> SEQUENCE: 76

Lys Lys Lys Lys Lys Ile Ile Ile Ile Ile Asp Asp Asp Asp Asp
1               5                   10                  15

<210> SEQ ID NO 77
<211> LENGTH: 15
<212> TYPE: PRT
<213> ORGANISM: Artificial
<220> FEATURE:
<223> OTHER INFORMATION: Synthetic peptide D2

<400> SEQUENCE: 77

Lys Lys Lys Lys Lys Ile Ile Ile Ile Ile Lys Asp Asp Asp Asp
1               5                   10                  15

<210> SEQ ID NO 78
<211> LENGTH: 15
<212> TYPE: PRT
<213> ORGANISM: Artificial
```

```
<220> FEATURE:
<223> OTHER INFORMATION: Synthetic peptide D3

<400> SEQUENCE: 78

Lys Lys Lys Lys Lys Ile Ile Ile Ile Ile Lys Lys Lys Asp Asp
1               5                   10                  15

<210> SEQ ID NO 79
<211> LENGTH: 15
<212> TYPE: PRT
<213> ORGANISM: Artificial
<220> FEATURE:
<223> OTHER INFORMATION: Synthetic peptide D8

<400> SEQUENCE: 79

Lys Lys Lys Lys Lys Ile Ile Ile Ile Ile Asp Asp Asp Asp Lys
1               5                   10                  15
```

SYNTHETIC ARTIFICIAL PEPTIDES WITH ANTIMICROBIAL EFFECT

The present invention relates to peptides with antimicrobial effect, to the medical use thereof, and to conjugates and compositions comprising such peptides.

The control and treatment of bacterial infections is a central theme in healthcare. Over past decades, the intensive use of antibiotic active ingredients in human medicine, veterinary medicine and agriculture has increasingly led to the formation of antibiotic-resistant germs. Such (multi) resistant germs nowadays present modern healthcare with major problems both in medical terms and also from an economic point of view.

In the search for alternatives to conventional antibiotics, in recent years antimicrobial or bactericidal peptides (AMPs) have become the focus of scientific and medical interest (Marr et al. 2006, Gordon et al. 2005). A series of naturally occurring peptides with antibacterial effect is known (Brogden et al. 2003, Diamond 2001, Lehrer and Ganz 2002, Tossi et al. 2000). These antimicrobial peptides sometimes have major differences in their sequence, the antimicrobial properties being connected essentially with two different modes of action. A bactericidal effect is known of peptides which, on account of a characteristic conformational acceptance, associate with biological membranes and, for example, lead to membrane permeabilization (Shai 1999). A bacteriostatic effect is attributed to those peptides which, as a result of interaction with cell-internal components, for example enzymes, cause a corresponding functional loss of metabolic key components (Gennaro and Zanetti 2000, Brotz et al. 1998, Subbalakshmi and Sitaram 1998, Otvos et al. 2000, Hilpert et al. 2010, Brogden 2005).

However, it has proven to be disadvantageous that natural antimicrobial peptides often have strong cytotoxic properties (Conlon et al. 2003, Ahmad et al. 2009, Ginsburg and Koren 2008). Also, natural AMPs, on account of their often complex structure, are burdened with high production costs and often weak pharmacokinetic properties (Zaiou 2007, Giuliani et al. 2007, Oyston et al. 2009), meaning that there is only a limited commercial and clinical benefit. The therapeutic use of natural antimicrobial peptides could moreover constitute a fundamental health risk because resistances to the closely related antimicrobial peptides of the innate immune system would possibly be promoted and, as a result, the natural immune defense to bacterial infections would be dangerously weakened (Bell and Gouyon 2003).

An alternative concept is the development of non-naturally occurring peptides with antimicrobial properties. A research focus here is the design of alpha-helical peptides since this structural motif is often connected with the antimicrobial properties of natural AMPs (Dathe 1997). One disadvantage of alpha-helical peptides is that, besides their effective antimicrobial effect, they often also have marked cytotoxic properties toward eukaryotic cells (Dathe 1997, Wiradharma 2013).

A much less widespread structural motif of antimicrobial peptides is the amphiphatic beta sheet. The design of beta sheet peptides with antimicrobial effect usually includes an alternating arrangement of hydrophobic and hydrophilic amino acids (Ong et al. 2013, Rausch et al. 2005, Rausch et al. 2007, Jin et al. 2005).

Despite intensive research efforts, the antimicrobial peptides known hitherto have disadvantages. In particular, an inadequate antimicrobial effect, a low activity spectrum, cytotoxic secondary effects, limited effect-kinetic and/or pharmacokinetic properties, and high production costs constitute limiting factors.

A problem to be addressed by the present invention therefore consists in providing peptides with improved properties as regards one or more of the aforementioned disadvantages.

Further objects addressed by the invention consist in indicating a medical use of the peptides, and also conjugates and antibacterial compositions comprising the peptides.

This aim is achieved according to the invention by an isolated peptide according to claim 1. Advantageous embodiments and uses of the isolated peptide are the subject of further claims.

The present invention is based on the development of an artificial peptidic structure principle which permits the synthesis of unusual and surprisingly simple AMPs with a high antimicrobial effect that is sometimes superior to that of known and natural peptides. It is of particular advantage here that the peptides according to the invention have a broad activity spectrum toward gram(−) and gram(+) bacteria and at the same time have a highly selective effect against bacterial cells, i.e. they have no or only very slight cytotoxic properties.

The basic structure of the peptides according to the invention is characterized by an N-terminal region A and a C-terminal region C with in each case predominantly basic amino acids, between which is arranged a central region B with predominantly hydrophobic and/or nonpolar amino acids.

In one embodiment of the invention, the isolated peptide is indicated by the general formula $$A_x B_y C_z.$$

Herein, A and C are the flanking regions with predominantly basic amino acids, where x and z are the number of amino acids in the region A or C, respectively. B is the central region with predominantly hydrophobic and/or nonpolar amino acids. Accordingly, y characterizes the number of amino acids in the region B.

The embodiments of regions A, B and C can vary for example as regards chain length and amino acids present, where x and z are greater than or equal to 1 and y is greater than or equal to 3. The total number of amino acids x+y+z in the peptide is less than or equal to 50, less than or equal to 35 or less than or equal to 25. In particular, however, the structural motif according to the invention also permits the realization of very short peptides with high antimicrobial effect. For example, the total number x+y+z of the amino acids can be less than or equal to 20, less than or equal to 18 or less than or equal to 16. In this way, a maximized antimicrobial effect is particularly advantageously combined with a simple and economic production.

A and C have, in each case independently of one another, at least 65%, at least 75% or at least 80% basic amino acids. A and C can, in each case also independently of one another, have at least 90% or at least 95% basic amino acids or consist exclusively of basic amino acids.

B has at least 65%, at least 75% or at least 80% hydrophobic and/or nonpolar amino acids. B can also have at least 90% or at least 95% hydrophobic and/or nonpolar amino acids or consist exclusively of hydrophobic and/or nonpolar amino acids.

In particular, there is a direct sequence of at least 3, 4 or 5 hydrophobic and/or nonpolar amino acids present in B. A direct sequence for the purposes of the invention is present if no further amino acids, for example polar amino acids, are arranged between the hydrophobic and/or nonpolar amino acids.

A peptide in the context of the invention is fundamentally present if the amino acid sequence of a peptide in a sensible interpretation produces at least one natural solution for x, y and z, in which the formula $A_xB_yC_z$ satisfies the aforementioned features. x, y and z are natural numbers. The formula is to be understood as meaning that no further regions are present besides the regions A, B and C.

In certain developments, A and/or C, independently of one another, contain at most one or no acidic amino acids. Alternatively or additionally, A and/or C, independently of one another, contain at most one or no hydrophobic amino acids.

In certain developments, B contains at most two, one or no acidic amino acids. Alternatively or additionally, B contains at most one or no basic amino acids.

As is generally customary in the specialist field, in the context of the present invention, alanine, valine, methionine, leucine, isoleucine, proline, tryptophan and phenylalanine are to be understood as meaning hydrophobic or nonpolar amino acids. Accordingly, basic amino acids are lysine, arginine and histidine. By contrast, the amino acids tyrosine, threonine, glutamine, glycine, serine, cysteine and asparagine are neutral or polar. Glutamic acid and aspartic acid are acidic amino acids. Hereinbelow, the amino acids are also referred to in the generally adopted single- or three-letter code (Stryer 1999).

It is clearly evident to the person skilled in the art that the invention is not limited to proteinogenic amino acids. In particular, the isolated peptide can also comprise corresponding non-proteinogenic amino acids. For example, the corresponding D-enantiomers, diastereomers, beta- or gamma-amino acid derivatives of proteinogenic amino acids can be present. Nonlimiting examples are D-Val, D-Leu, D-Ile, D-Phe, D-Lys and D-Arg. Furthermore, the isolated peptide can also comprise synthetic building blocks, for example with corresponding basic, for example alpha-amino-3-guanidinopropionic acid, or hydrophobic or non-polar properties, for example norleucine, and also carbamate compounds. Preferably, these are integrated into the peptide sequence via at least one amide bond. It is also possible to configure the C terminus and/or N terminus of the peptide amidated or acetylated. In this way, it is for example possible to provide peptides with improved pharmacokinetic properties and/or a lower risk of resistance developments since they have largely been taken from the natural recognition and degradation mechanisms.

In a preferred embodiment, the hydrophobic and/or nonpolar amino acids, independently of one another, are selected from the group consisting of valine, leucine, isoleucine, phenylalanine and any desired combinations thereof. Particularly preferred hydrophobic and/or nonpolar amino acids are valine, leucine, isoleucine and any desired combinations thereof. The inventors were able to establish that such peptides have particularly good antimicrobial properties and at the same time a low cytotoxic effect.

In a further preferred embodiment, the basic amino acids are selected, independently of one another, from lysine and arginine and combinations thereof. Particular preference is given to lysine. In this way, for example, the selectivity toward microbial cells can be increased and the cytotoxicity reduced.

The number x of amino acids in the amino-terminal region A is preferably $x \geq 2$ or $x \geq 3$. Alternatively or additionally, the number z of amino acids in the carboxy-terminal region C is greater than or equal to 2 or greater than or equal to 3. In a preferred development, moreover, x and z, in each case independently of one another, are less than or equal to 12, less than or equal to 9 or less than or equal to 7.

Typically, the region B has a number y of greater than or equal to 4 or greater than or equal to 5 amino acids. In certain embodiments, it is envisaged that the total number y of amino acids in the central region B is less than or equal to 20, less than or equal to 15 or less than or equal to 10. In these embodiments, for example a particularly good antimicrobial effect against gram(−) negative bacteria is achieved.

In certain embodiments, the N-terminal amino acid in A is a basic amino acid. Alternatively or additionally, the C-terminal amino acid in C is a basic amino acid. Using such peptides, the inventors were able to achieve particularly good antimicrobial properties.

Preferably, the peptide is configured at least partially as beta strand in an aqueous medium. The inventors were able to establish that there is a direct connection between the beta strand content of the peptides according to the invention and their antimicrobial effectiveness. This is surprising insofar as beta sheet motifs known hitherto in antimicrobial peptides usually require an alternating sequence of hydrophobic amino acids and hydrophilic, uncharged or charged amino acids (see for example Rausch et al. 2007; Ong et al. 2013). By contrast, the inventors succeeded in forming unusual beta strand peptides via the present structural motif. In this way, shorter peptides and/or simpler peptides as regards the amino acid composition with antimicrobially effective beta structure can be provided.

Suitable methods for determining the beta strand content of the peptides according to the invention are explained in example 8. Alternative analytical methods such as, for example, circular dichroism or infrared spectroscopy are sufficiently known to the person skilled in the art (Lottspeich and Engels 2006; Richter 2003).

In particular, peptides with a high beta strand content can be realized with the structure according to the invention. The inventors were able to demonstrate that a high beta strand content in the peptides according to the invention correlates with a high antimicrobial effect and low cytotoxicity. In preferred embodiments, therefore, at least 50%, 65%, 75% or 85% of the amino acids of the peptide are comprised in a single beta strand. In this way, peptides are provided which destroy bacterial membranes even in low concentrations and/or within a short time.

In a further preferred embodiment, the peptide is present as stretched beta strand. A stretched beta strand in the context of the invention is present particularly if the peptide forms a continuous beta strand which is not interrupted by a beta hairpin, alpha-helix and/or unstructured region. Since in the prior art the pore-forming property of AMPs has hitherto been connected only with a beta sheet structure in which at least two beta strands of a peptide spatially interact via a beta hairpin (Rausch et al. 2005; Rausch et al. 2007), it offers unexpected advantages that such structures are not required in the peptides according to the invention. For example, significantly shorter and thus more economical AMPs can be provided which sometimes have even higher antimicrobial activity than the conventional beta sheet structured AMPs.

In certain embodiments, the peptide according to the invention, moreover, has no alpha-helix in an aqueous medium. By avoiding alpha-helical motifs in the peptide, cytotoxic secondary effects of the AMPs can be effectively avoided according to the invention.

According to a further embodiment, the peptide on the C terminus is configured as carboxamide. The inventors were surprisingly able to establish that a further improvement in the antimicrobial properties is achieved with the help of an amidation of the carboxy terminus compared to the corresponding free carboxylic acid of the peptides according to the invention.

In a further embodiment of the invention, the peptide has a number x or a number z of amino acids in the amino-terminal region A or carboxy-terminal region C of $3 \leq x \leq 7$ or $3 \leq z \leq 7$. At the same time, the peptide has a number y of amino acids in the in between region B of $5 \leq y \leq 10$. Accordingly, in any desired combination and independently of one another, x and z can be in each case 3, 4, 5, 6 or 7 and y can be 5, 6, 7, 8, 9 or 10. In a preferred development of this embodiment, the amino acids of A and C, independently of one another, are selected from the group consisting of lysine and arginine, and also combinations of these amino acids. Furthermore, the amino acids of B are selected from the group consisting of valine, leucine, isoleucine and phenylalanine, and combinations of these amino acids. In these embodiments, the peptides according to the invention combine particularly high antimicrobial effectiveness and a broad activity spectrum with minimal cytotoxicity. At the same time, a particularly economic manufacture is ensured on account of the shortness of the sequence.

In one embodiment, the peptide has a minimum inhibitory concentration (MIC) toward gram(−) bacteria of less than or equal to 32 µM, less than or equal to 16 µM, less than or equal to 8 µM, less than or equal to 4 µM, less than or equal to 2 µM, less than or equal to 1 µM or less than or equal to 0.5 µM. Alternatively or additionally, the peptide can have a minimum inhibitory concentration (MIC) toward gram(+) bacteria of less than or equal to 32 µM, less than or equal to 16 µM, less than or equal to 8 µM, less than or equal to 4 µM, less than or equal to 2 µM, less than or equal to 1 µM or less than or equal to 0.5 µM. A suitable method for determining the MIC is described below in example 2.

In a further embodiment of the invention, the peptide has the ability to permeabilize the membrane of gram(+) bacteria above a peptide concentration of 50 µM, 25 µM or 5 µM. Alternatively or additionally, the peptide has the ability to permeabilize the membrane of gram(−) bacteria above a peptide concentration of 50 µM, 25 µM or 5 µM. A suitable method for determining the membrane-permeabilizing peptide concentration is described in example 4.

The $LD_{50}$ toward eukaryotic cells of the peptide is preferably at a concentration greater than or equal to 50 µM, greater than or equal to 60 µM or greater than or equal to 64 µM. A suitable method for determining the $LD_{50}$ value is explained in example 6. Such peptides are particularly suitable for therapeutic antibiosis on account of low cytotoxic side effects.

A further aspect of the invention relates to a conjugate comprising the peptide described previously. A conjugate in the context of the invention is a material comprising the peptide and at least one further component. The further component has at least one deviating property compared to the peptide, which is typically a physical, structural and/or (bio)chemical property. As a result, the conjugate according to the invention is at least in part given different properties than its individual components each taken by themselves. In particular, the peptide is present covalently and/or adsorptively coupled to the further component. The further component can comprise, for example, a (signal) peptide, a protein, a nucleic acid, a lipid or a saccharide. The further component can also comprise a particle such as, for example, an organic or inorganic nano- or microparticle. In this way, different advantageous effects can be achieved with the conjugate according to the invention, for example an improved bioavailability and/or biocompatibility, a targeted or selective accumulation or release of the peptide at the desired site of action.

The further component can also comprise natural and/or synthetic polymers. Suitable polymers are, without limitation, polyethylene glycols (PEG), acrylates, epoxides, urethanes, cellulose derivatives, polyesters, polystyrene and polyvinyl polymers, silicones, parylenes and combinations thereof. Furthermore, functionalized surfaces such as, for example, glass-, plastic- or metal-comprising surfaces, are provided as further component.

A further aspect of the invention relates to the medical use of the peptide described previously as medicament. In particular, the medical use of the peptide for treating bacterial infections is provided. Such a bacterial infection can for example include a multiresistant germ. On account of the high selectivity, low cytotoxicity in antimicrobial concentrations and the broad activity spectrum, the peptides according to the invention are particularly advantageous for use as broad-spectrum antibiotics in a wide application area of local, systemic or external therapeutic applications and for overcoming bacterial multiresistances.

It is also possible to use the peptide in combination with a further antimicrobial active ingredient. In particular, the use in combination with an antibiotic selected from the group of beta-lactams, glycopeptides, polyketides, aminoglycosides, polypeptide antibiotics, quinolones, sulfonamides and combinations thereof is provided. It is advantageous that the peptides according to the invention have a different mechanism of action compared to conventional antibiotics so that a synergy effect of the two active ingredient classes arises which is particularly well suited for treating bacterial infections, in particular with germs that are already antibiotic-resistant. In this way, such antibiotics can also find a new medical use against which resistances have already been developed.

In a further aspect of the invention, an antimicrobial composition comprising the peptide described above is provided. An antimicrobial composition can be a pharmaceutical composition. The pharmaceutical composition preferably comprises a therapeutically effective amount of the peptide. The pharmaceutical composition can inter alia comprise auxiliaries. Such auxiliaries can comprise for example lactose, cellulose, starch, sucrose, paraffin, hard fat, polyethylene glycol and/or polyethylene oxide, and derivatives thereof. The pharmaceutical composition can also comprise a protease inhibitor. The pharmaceutical composition can be provided for local, systemic or external application. The pharmaceutical composition can in particular also comprise a further antibiotic as already described previously.

In another embodiment, the antimicrobial composition is a coating, for example an antifouling coating. Such coatings can be used for example at interfaces in order to prevent or to control the colonization of microorganisms, so-called biofilms. In one embodiment, the coating of medical equipment is provided. A nonlimiting example of this is the coating of medical implants, for example of endoprostheses, catheters, tubes or stents. In another embodiment, the coating of surfaces exposed to water or weathering is provided, for example of boat hulls, pipelines or glazings. The coating can also relate to textile products, for example clothing, surgical drapes or bedding.

In certain embodiments, the peptide has at least 90% or at least 95% sequence homology with one of the peptides of the SEQ ID NO: 1 to SEQ ID NO: 49. The percentage sequence agreement between two peptide sequences can be determined for example with the help of the "ClustalW" algorithm by Thompson et al. (1994).

Preferably, the peptide is produced synthetically, for example in chemical solid-phase synthesis (SPPS). Particular preference is given to chemical solid-phase synthesis on a synthesis resin which has an amide linker. In this way, the peptide is present after being cleaved off from the resin in the form of the carboxamide which has particularly good antimicrobial properties. At the same time, the peptide is better protected against a proteolytic degradation as a result of the amidation, which is advantageous for use as a therapeutic. By means of this process it is possible to produce the peptide in a particularly simple and economic manner.

BRIEF DESCRIPTION OF THE SEQUENCES

SEQ ID NO: 1 to SEQ ID NO: 49 are peptides according to the invention.
SEQ ID NO: 50 to SEQ ID NO: 79 are reference peptides.
In the examples which follow, certain embodiments of the invention are described in more detail by reference to figures and experimental data. The examples and figures do not serve as a limitation to specific details.

Example 1

Antimicrobial Peptides

For the analysis, natural antimicrobial reference peptides from various sources were analyzed. Melittin extracted from honeybee toxin was acquired in a purity of more than 85% via Sigma-Aldrich (Taufkirchen, Germany). Protamine from salmon was acquired in grade IV quality histone-free likewise via Sigma-Aldrich. The peptides indolicidin, BMAP-27, the alpha-helical KL peptide, and also the library of the peptides according to the invention and comparison peptides were acquired per custom synthesis from JPT Peptide Technologies GmbH (Berlin, Germany). Unless stated otherwise below, the peptides were produced as free acid (COOH) on the C-terminus. The peptides according to the invention can advantageously be produced in a particularly simple and economic manner in solid-phase synthesis. Quality control of the peptides was carried out with HPLC/MS analysis. For the investigations below, the peptides were used in a purity of at least 70%. All of the peptides were stored in a lyophilized state at −20° C. and dissolved in deionized water only prior to use in a concentration of 2 mM.

Example 2

Determination of the Minimum Inhibitory Concentration (MIC)

Figure 1:
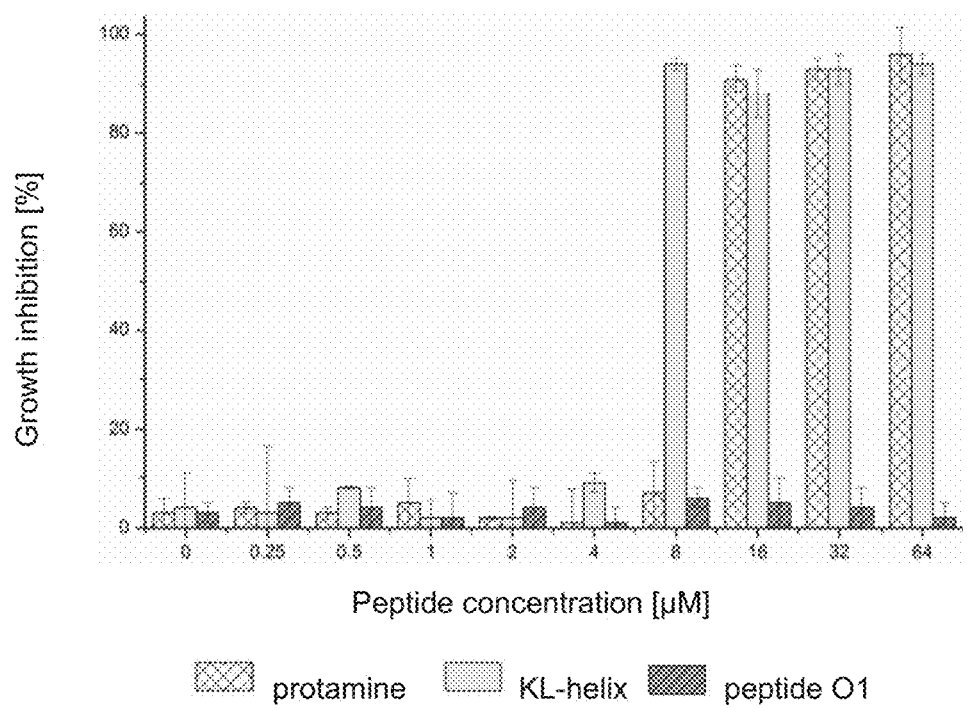
FIG. 1 shows a representative evaluation example for determining the minimum inhibitory concentration (MIC). In the bar graph, the growth inhibition is shown as a percentage over the corresponding peptide concentration in µM by way of example with reference to the reference peptides protamine (SEQ ID NO: 52), KL-helix (SEQ ID NO: 54) and the peptide O1 (SEQ ID NO: 27) according to the invention.

The minimum inhibitory concentration (MIC) of the peptides was carried out by way of example against gram(−) E. coli DH5α (and gram(+) Staphylococcus xylosus (both Deutsche Sammlung von Mikroorganismen und Zellkulturen, DSMZ) in a standardized microdilution method according to the general guidelines of the CLSI (Clinical and Laboratory Standards Institute 2006) and EUCAST (European Committee for Antimicrobial Susceptibility Testing of the European Society of Clinical Microbiology and Infectious Diseases 2003) with slight adaptations to the investigation of cationic antimicrobial peptides (Wiegand et al. 2008). The bacteria cells were cultivated in Mueller-Hinton-Boullion (MHB) to an optical density of 0.4 to 0.6 at 600 nm wavelength, corresponding to about $4 \cdot 10^8$ bacteria per ml. Then, the bacteria cultures were diluted to a bacteria concentration of about $1 \cdot 10^5$ bacteria per ml in sterile MHB. Using the peptides, series of 2-fold dilutions starting at 128 µM to the smallest dilution of 0.5 µM in MHB were prepared. The peptide dilutions were mixed with the dilute bacteria cultures in a 1:2 volume ratio in the chambers of a 96-well polypropylene microtiter plate (Starlab, Hamburg, Germany), so that the peptides were present in an end concentration between 64 µM and 0.25 µM at a bacteria concentration of $5 \cdot 10^4$ bacteria/ml. Sterile MHB served as negative control, and the positive control used as the corresponding bacteria concentration in MHB without the addition of peptide. The microtiter plates were incubated for 18 hours at 37° C. with shaking at 120 rpm in a climatically controlled chamber. After the incubation, the bacteria concentration was determined by renewed absorption measurement at a wavelength of 600 nm. The MIC determined was the lowest peptide concentration at which no difference in the absorption could be established between the sample and the positive control. A representative evaluation is shown in FIG. 1.

Example 3

Flow Cytometric Determination of Cell Viability

Figure 2:
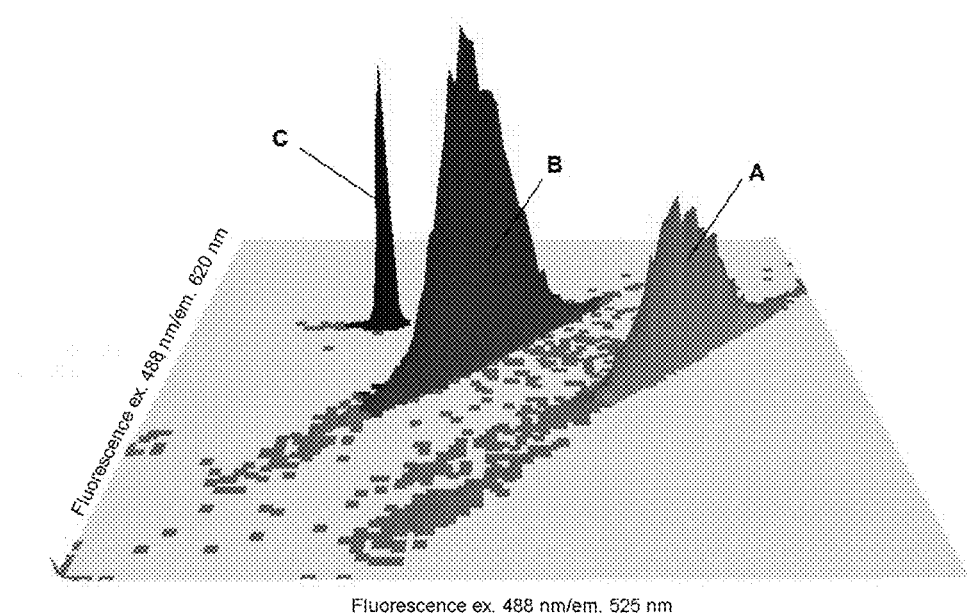
FIG. 2 shows by way of example a dotplot of a flow cytometric measurement of a sample with about 50% living (A) and 50% dead bacteria (B), and calibration particles (C).

Destruction of the bacteria membranes by the antimicrobial peptides was investigated in a flow cytometric method with the help of a living/dead staining method in combination with an internal calibration and counting system. For this purpose, SYBR Green I (Sigma-Aldrich) was used as total staining and propidium iodide (Sigma-Aldrich) was used as contrast staining for membrane-damaged bacteria. The calibration and quantification of the measurement method was achieved with the help of PeakFlow Orange Flow Cytometry Reference Beats (Life Technologies, Darmstadt, Germany). The flow analysis was carried out on a Cytomics FC500 Instrument (Beckmann Coulter, Munich, Germany) equipped with an argon laser (488 nm) and the corresponding emission filters for SYBR Green I (525 nm) and propidium iodide (620 nm). All of the detectors were adjusted to a log-ten scale and the gates were prejustified by means of preliminary experiments with living and isopropanol-killed bacteria. Optical and electronic noise was eliminated by means of the prejustification of a threshold value to the forward scattered light detector. The flow rate was held at approximately in the range of 300 events per second. The total measurement capture was 20 000 events. Prior to the sample analysis, the dyes, calibration particles and carrier liquid were combined in a mastermix. For a measurement, 50 µl of bacteria culture were added to 450 µl of mastermix so that end concentrations of 10 µM propidium iodide, 2-fold SYBR Green I and $1.2 \cdot 10^5$ particles/ml were present. Then, the mixture was incubated for 10 min in the dark at room temperature and then measured by flow cytometry. The number of events in each gate was captured and evaluated using the CXP Analyses 2.2 Software. The total number of living and dead bacteria was calculated. Events which could be assigned neither to a living nor a dead bacteria cell were excluded from the calculation. An exemplary dotplot as the result of the flow cytometric measurement of a sample with about 50% living bacteria (A) and 50% dead bacteria (B) and also calibration particles (C) is shown in FIG. 2.

Example 4

Figure 3:
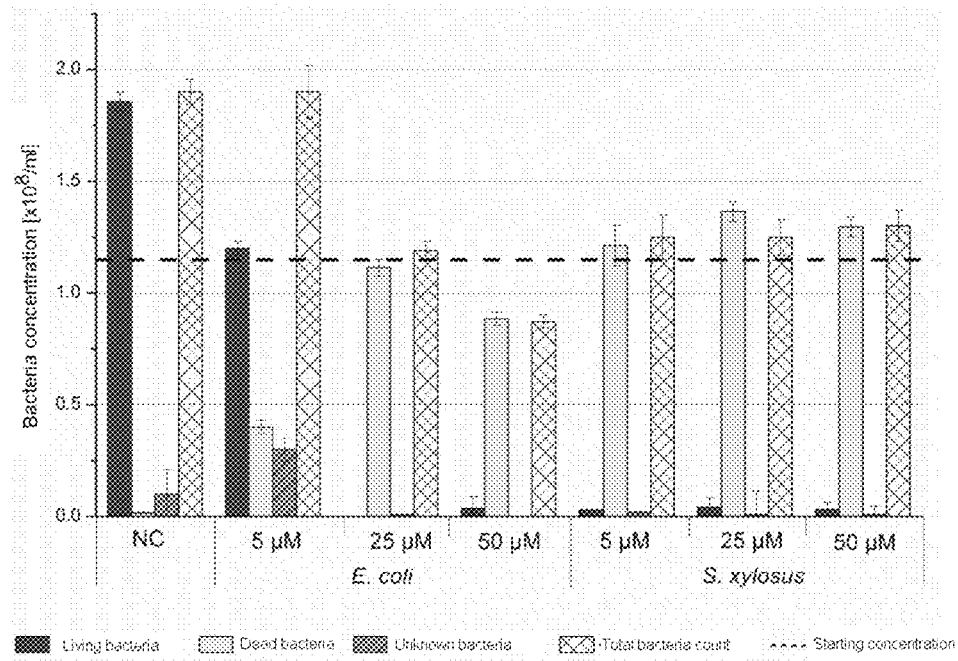
FIG. 3 shows by way of example the numerical evaluation of a flow cytometric measurement for determining the membrane-permeabilizing properties of the antimicrobial peptides by reference to the peptide O1 according to the invention. In the bar graph, the bacteria concentration is plotted separately broken down into living, dead, unknown and total bacteria over the respective peptide concentration for *Escherichia coli* (*E. coli*) and *Staphylococcus xylosus* (*S. xylosus*).

Determination of the Permeabilizing Properties of the Antimicrobial Peptides Toward Bacteria Membranes For the determination of the depolarizing properties of the antimicrobial peptides, in each case three different peptide concentrations were tested by way of example against gram(−) E. coli DH5α (and gram(+) Staphylococcus xylosus. The bacteria were cultivated in MHB to an optical density of 0.4 to 0.6 at 600 nm, corresponding to about $4 \cdot 10^8$ bacteria/ml. Then, the bacteria concentration was adjusted to about $2 \cdot 10^8$ bacteria/ml in MHB using flow cytometry. The antimicrobial peptides were diluted in MHB and added to the bacteria culture such that final peptide concentrations of 50 µM, 25 µM and 5 µM in combination with a final bacteria concentration of $1 \cdot 10^8$ bacteria/ml was present. Accordingly, the samples were incubated firstly for 2 hours at 37° C. with gentle shaking. Then, the bacteria were analyzed by flow cytometry as described in Example 3. The lowest peptide concentration was established at which at least 80% of the bacteria population had permeablized membranes. A representative example result is shown in FIG. 3 for the peptide O1. In the bar graph, in each case the ascertained number of living, dead, unknown and total bacteria is shown separately according to E. coli and S. xylosus as a function of the peptide concentration used. As comparison parameter, the corresponding bacteria concentrations in the negative control (NC) are shown.

Example 5

Investigation of the Permeabilization of the Outer and Inner Bacteria Membrane

Figure 4:
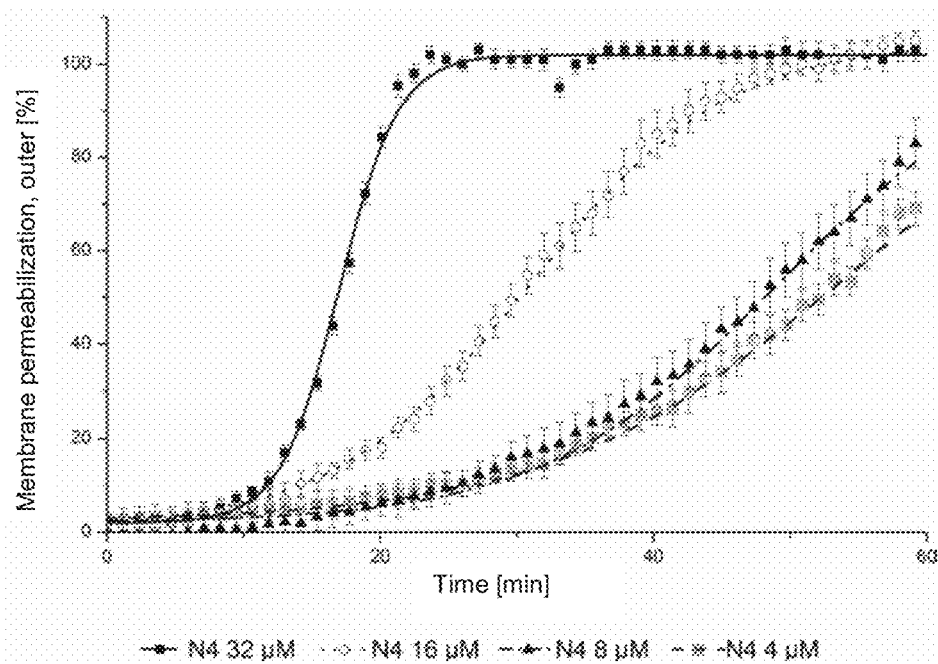
FIG. 4 shows an exemplary graphical evaluation for the kinetic analysis of the membrane permeabilization by reference to the measurement values of the peptide N4 (SEQ ID NO: 2) according to the invention for the outer bacteria membrane.
Figure 5:
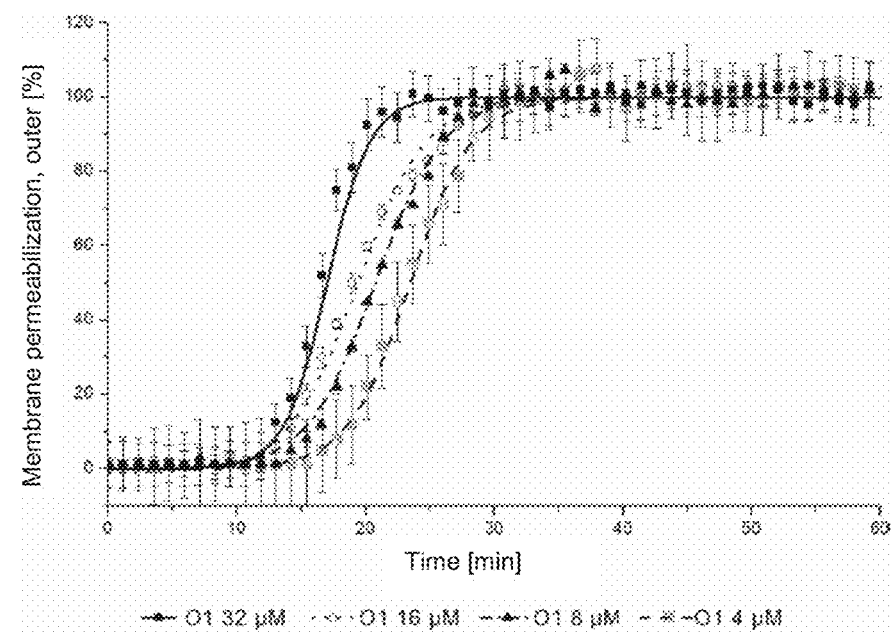
FIG. 5 shows by way of example the graphical evaluation for the kinetic analysis of the membrane permeabilization by reference to the measurement values of the peptide O1 (SEQ ID NO: 27) according to the invention for the outer bacteria membrane.

The ability of the antimicrobial peptides for the respective permeabilization of the outer and inner bacteria membrane was tested by way of example on E. coli ML-35p (made available by Dr. R. E. Lehrer, Center for Health Sciences, Los Angeles, Calif., USA). The peptides were incubated in serial dilution with E. coli ML-35p and the time-dependent release of cell-internal components was measured in a slightly modified protocol according to Ericsson et al. (2002). For this purpose, the bacteria were cultured in Luria-Bertani (LB) medium with 100 µg/ml ampicillin (Fluka, Taufkirchen, Germany) until reaching an optical density of 0.4 at 600 nm wavelength. Then, the cells were washed three times by centrifugation at 4000 g for 1 min and subsequent up-take in 10 mM HEPES buffer pH 7.2. Finally, the cells were diluted to an optical density of 0.3 at 600 nm wavelength. To measure the permeabilization of the outer membrane, nitrocefin (Merck, Darmstadt, Germany) was diluted in HEPES buffer to a concentration of 60 µg/ml. The antimicrobial peptides were diluted in HEPES buffer to an end concentration of 12 µM, 24 µM, 48 µM and 96 µM end concentration. In the next step, 50 µl of nitrocefin were admixed with 50 µl of antimicrobial peptide and 50 µl of bacteria suspension such that an end concentration of 20 µg/ml of nitrocefin, 4 µM to 32 µM of antimicrobial peptide and bacteria with an optical density of 0.1 to 600 nm were present. The samples were mixed and the absorption at 500 nm wavelength was measured directly over a period of at least 90 min at 37° C. with regular shaking in a FLUOstar omega Microplate Reader (BMG Labtech, Ortenberg, Germany). The investigation of the permeabilization of the inner membrane was carried out in the same way except that instead of the nitrocefin accordingly 0-nitrophenyl-beta-D-galactoside (ONPG, Sigma-Aldrich) in an end concentration of 100 µg/ml was used and the absorption change was determined at a wavelength of 420 nm. The control used was samples without antimicrobial peptide, the positive control used for the membrane permeabilization was polymyxin B (Sigma-Aldrich) in an end concentration of 5 µM. For the data evaluation, firstly the measurement values of the corresponding negative controls were deducted from the measurement values of the samples, and the difference was then divided by the corresponding measurement values of the permeabilization control. Then, a graphical evaluation was carried out, the calculated values being plotted against the peptide concentration and being fitted with the help of the Origin Pro 8.1 G Software (OriginLab) according to a sigmoidal model. As representative examples, FIGS. 4 and 5 show the graphical evaluation for the kinetic investigation of the permeabilization of the outer *E. coli* bacteria membrane for the peptides N4 (FIG. 4) and O1 (FIG. 5).

As comparison parameter between the peptides, the times were ascertained from this at which 50% of the final signal level was reached. For this purpose, the equation with the percentage membrane permeabilization y, the time x in minutes, the lower plateau A1, the upper plateau A2, the point of inflection Log X0 and the Hill incline p $$y = A1 + \frac{A2 - A1}{1 + 10^{(LogX_0 - x) \cdot p}} \quad (5.1)$$

was used. The calculation of the parameters A1, A2, Log X0 and p was performed by the program by reference to the compensating curve. Further resolution of equation 5.1 for the case y=50 then produced for x the desired time at which the half-maximum signal level was reached.

Example 6

Calculation of the Cytotoxicity and of the Therapeutic Ratio of the Antimicrobial Peptides The cytotoxic potential of the antimicrobial peptides was determined by way of example by reference to the human histiocytic lymphoma cell line U937 (DSMZ). The influence of the peptides on the permeability of the cell membrane and their longer-term growth-inhibiting effect was investigated. 15 ml of RPMI 1640 medium with 2 mM glutamine and 10% FCS (Biochrom, Berlin, Germany) were inoculated with $1 \cdot 10^5$ cells per ml and cultivated for three days at 37° in T75 cell culture bottles (TPP, Trasadingen, Switzerland) with constant gassing with 5% $CO_2$ in a climatically controlled chamber. The medium was admixed with 10 U/ml penicillin and 100 mg/ml streptomycin (both AppliChem, Darmstadt, Germany) to avoid bacterial contaminations, with no further antibiotics being added during the subsequent recultivation. Before each experiment, the cells were washed by centrifugation at 100 g for five minutes and subsequent resuspension in RPMI 1640 medium with 2 mM glutamine and 10% FCS in each case two times and adjusted to a concentration of $1 \cdot 10^5$ cells per ml. Finally, in each case 100 µl of the U937 cells were transferred to the reaction chambers of a sterile 96-well polypropylene microtiter plate and admixed with in each case 100 µl of a prediluted antimicrobial peptide in RPMI 1640 medium without antibiotic addition, such that end concentrations of in each case $5 \cdot 10^4$ cells per ml at peptide concentrations between 0.25 µM and 64 µM were present. The negative control used was samples without antimicrobial peptide, while Triton X-100 (AppliChem) was used in an end concentration of 5% as positive control for the permeabilization. The samples were cultivated for two hours at 37° C. and with continuous gassing with 5% $CO_2$ in a climatically controlled chamber. Then, in each case 100 µl of each sample were removed and transferred to new sterile microtiter plates for determining the direct membrane damage. The remaining 100 µl of the samples were cultivated for at least four further days.

Figure 6:
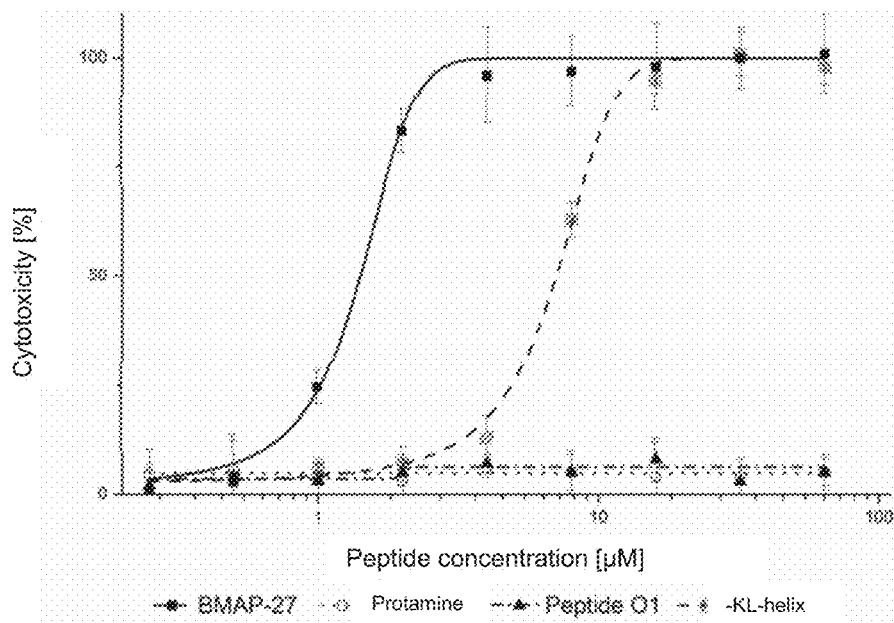
FIG. 6 shows representative graphical evaluations for determining the cytotoxicity by reference to the reference peptides BMAP-27 (SEQ ID NO: 51), protamine (SEQ ID NO: 52), KL-helix (SEQ ID NO: 54) and the peptide O1 (SEQ ID NO: 27) according to the invention.

The direct membrane damage was investigated with the help of the CytoTox 96 Non-Radioactive Cytotoxicity Assay (Promega, Mannheim, Germany). For this purpose, the cells were sedimented at 100 g for ten minutes at 4° C., and 50 µl of the resulting culture supernatant were added to 50 µl of the CytoTox substrate mix. After an incubation time of 30 minutes in the dark at room temperature, 50 µl of the CytoTox stopping solution were added to the sample and the absorption was measured at 490 nm. To determine the $LD_{50}$ value, the measurement value of the negative control was deducted from the absorption values and divided by the measurement value of the permeabilization control. The calculated values were plotted graphically against the peptide concentration and fitted using the Origin pro 8.1 G Software according to a sigmoidal model and the $LD_{50}$ values were ascertained from this. The calculation was carried out analogously to example 5 by reference to the solution of equation 5.1 for the case y=50, where y in this case corresponds to the relative cytotoxicity in percent and x corresponds to the peptide concentration in µM. Representative graphical evaluations of $LD_{50}$ values are shown in FIG. 6 by reference to the measurement results for the reference peptides BMAP-27, protamine and KL-helix, and also the peptide O1 according to the invention.

The therapeutic ratio corresponds to the quotient of the $LD_{50}$ value and the MIC value of a peptide. In those cases in which the $LD_{50}$ value was above the measured peptide concentrations, an $LD_{50}$ of 128 µm was used as the basis for calculating the therapeutic ratio.

A high therapeutic ratio is accordingly advantageous because it corresponds to a high antimicrobial activity coupled with simultaneously slight cytotoxic side effects of the antimicrobial peptide.

For the determination of the long-term growth inhibition of the antimicrobial peptides, the total cell numbers in the samples were determined after the further cultivation of a further four days had elapsed. For this purpose, 10 µl of lysing solution were added to in each case 100 µl of cell suspension and incubated for 60 minutes at 37° C. Then, the cell culture supernatants were investigated as described above. The lowest peptide concentration at which complete suppression of the cell growth was established after four days was stipulated as the minimum toxic concentration (MTC).

Example 7

Treatment of Bacterially Contaminated Cell Cultures

The ability of the antimicrobial peptides to be used as a therapeutic active ingredient was investigated by reference to its selective antimicrobial properties in model mixed culture experiments. For this purpose, the human cell line U937 and *Staphylococcus xylosus* were prepared as described in example 6 or example 2. Then, a mixed culture with $1 \cdot 10^6$ bacteria cells/ml and $1 \cdot 10^6$ U937 cells/ml, and either 25 µM or 50 µM antimicrobial peptide in RPMI 1640 medium was prepared. Sterile medium was used as negative control, whereas the antimicrobial peptide melittin was used as toxicity control. The mixed cultures were incubated with constant gassing with 5% $CO_2$ in a climatically controlled chamber for two hours at 37° C. Then, the mixed cell cultures were stained and measured by flow cytometry as described in example 3, the measurement scale being adapted to the measurement of the larger eukaryotic cells.

Example 8

Calculation of the Physico-Chemical Peptide Properties and Prediction of the Peptide Structure The hydrophobicity (H) and the hydrophobic moment (p) and also the helix wheel projection were calculated assuming an ideal alpha-helical conformation for each individual antimicrobial peptide. The calculation was carried out with the help of the HeliQuest Webserver (Gautier et al. 2008) assuming a neutral medium at pH 7.4. The most probable three-dimensional structure of the peptides was calculated assuming an aqueous medium with the help of the PEP-FOLD Webserver (Thévenet et al. 2012, Maupetit et al. 2010, Maupetit et al. 2009). Additionally, the ascertained three-dimensional structures were confirmed with the help of the PEPstr Peptide Tertiary Structure Prediction Webserver (Kaur et al. 2007), with a vacuum, an aqueous medium and a hydrophobic medium being used as the basis for the calculations. Peptides with fewer than nine amino acids were excluded from the calculation. The structure predictions were processed using the Geneious 6.1.5 Software (www.geneious.com) and visualized with the help of the UCSF Chimera Software (Pettersen et al. 2004). The graphical representation was carried out in the ribbon style model, with the alpha-helices being shown as coils and the beta strands being shown as arrows. The arrow tips point to the C terminus.

Example 8

Antimicrobial Properties of Natural Reference Peptides

As comparison parameter for the antimicrobial properties of the isolated peptides of the present invention, the antimicrobial properties of the four natural AMPs mellitin (SEQ ID NO: 50), BMAP-27 (SEQ ID NO: 51), protamine (SEQ ID NO: 52) and indolicidin (SEQ ID NO: 53), and also of the non-naturally occurring alpha-helix-forming KL peptide (SEQ ID NO: 54) were investigated. The results are summarized in table 1.

TABLE 1

Summary of the physico-chemical, antimicrobial and cycotoxic properties of the natural reference peptides. All of the values represent the arithmetic mean of the results from four independent test series.

| Peptide | Sequence[1] | Properties | | MIC [µM] | | Toxicity [µM] | | Therapeutic ratio[2] | |
|---|---|---|---|---|---|---|---|---|---|
| | | H | µ | E. coli | S. xylosus | $LD_{50}$ | MTC | E. coli | S. xylosus |
| Melittin | GIGAVLKVLTTGLPALISWIKRKRQQ (SEQ ID NO: 50) | 0.511 | 0.394 | 8 | 2 | 1.4 | 2.0 | 0.18 | 0.7 |
| BMAP-27 | GIGAVLKVLTTGLPALISWIKRKRQQ (SEQ ID NO: 51) | 0.380 | 0.456 | 1 | 2 | 1.8 | 4.0 | 1.80 | 0.9 |
| Protamine | MPRRRRSSSRPVRRRRRPRVSRRRRR RGGRRR (SEQ ID NO: 52) | -0.454 | 0.086 | 8 | 0.5 | >64 | 16 | (16) | (256) |
| Indolicidin | ILPWKWPWWPWRR (SEQ ID NO: 53) | 1.069 | 0.190 | 4 | 32 | >64 | >64 | 32 | 4 |
| KL-helix | LKLLKKLLKKLLKLL (SEQ ID NO: 54) | 0.624 | 0.836 | 4 | 2 | 7.0 | 8.0 | 1.75 | 3.5 |

[1]Sequence given as a single-letter code from the N terminus to the C terminus.
[2]Values in parentheses mean that an MTC was established but no $LD_{50}$.

The reference peptides have a general antimicrobial activity toward *E. coli* and *S. xylosus*, where the MIC values are between 1 µM and 8 µM or 0.5 µM and 32 µM. At the same time, the peptides melittin, BMAP-27 and KL-helix have strong cytotoxic properties toward the model cell line U937, the $LD_{50}$ values being between 1.4 µM and 7 µM. Since these values essentially correspond to the respective MIC values, a disadvantageous therapeutic ratio of approximately 1 is present. Only protamine and indolicidin have more advantageous therapeutic ratios on account of low cytotoxic properties, although protamine exhibits a questionable complete growth inhibition of eukaryotic cells already at a concentration of 16 μM.

Table 2 shows the corresponding membrane-destroying properties of the reference peptides. Whereas melittin, BMAP-27 and KL-helix destroy the bacteria membranes within a few minutes, in the case of indolicidin and protamine only slight or even no membrane destruction can be detected.

TABLE 2

Summary of the membrane-destroying properties of the natural reference peptides. All of the values represent the arithmetic mean of the results from four independent test series.

| Peptide | General permeabilization [μM] | | Outer membrane [min] | | | | Inner membrane [min] | | | |
|---|---|---|---|---|---|---|---|---|---|---|
| | E. coli | S. xylosus | 4 μM | 8 μM | 16 μM | 32 μM | 4 μM | 8 μM | 16 μM | 32 μM |
| Melittin (SEQ ID NO: 50) | 25 | 5 | 14 | 9 | 2 | <1 | 18 | 12 | 9 | 6 |
| BMAP-27 (SEQ ID NO: 51) | 5 | 5 | <1 | <1 | <1 | <1 | 16 | 9 | 7 | 5 |
| Protamine (SEQ ID NO: 52) | >50 | >50 | <1 | <1 | <1 | <1 | >90 | >90 | >90 | >90 |
| Indolicidin (SEQ ID NO: 53) | >50 | 50 | >90 | >90 | >90 | >90 | >90 | >90 | >90 | >90 |
| KL-helix (SEQ ID NO: 54) | 5 | 5 | 2 | <1 | <1 | <1 | 14 | 11 | 9 | 6 |

Figure 8:
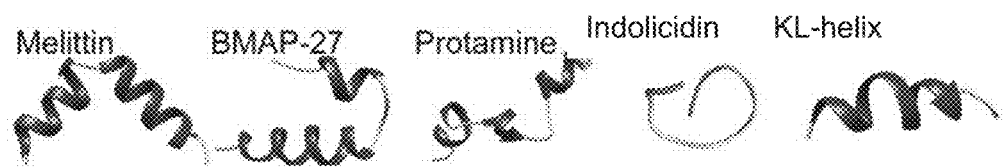
FIG. 8 shows models of the spatial structure of the natural reference peptides melittin (SEQ ID NO: 50), BMAP-27 (SEQ ID NO: 51), protamine (SEQ ID NO: 52), indolicidin (SEQ ID NO: 53) and KL-helix (SEQ ID NO: 54).

The peptides also have differences with regard to their physico-chemical properties and three-dimensional structures (FIG. 8). Melittin, BMAP-27, protamine and KL-helix form expanded alpha-helical regions whereas protamine has two short terminal alpha-helical regions and a large central unstructured region. By contrast, indolicidin has a less defined structure which results in a random coil conformation. The alpha-helical peptides melittin, BMAP-27 and KL-helix have a hydrophobicity between 0.38 and 0.624, and a hydrophobic moment between 0.394 and 0.836. Only indolicidin, with 1.069, has a higher hydrophobicity than the alpha-helical peptides. At the same time, indolicidin lacks amphipathicity, which is evident from the low hydrophobic moment of 0.19. By contrast, the largely unstructured protamine has neither high hydrophobicity nor high amphipathicity.

Example 9

Execution of the General Structural Motif

The antimicrobial effect of the peptidic structural motif $A_xB_yC_z$ according to the invention was investigated by way of example by reference to a representative peptide M1 according to the invention (SEQ ID NO: 1) and also five reference peptides M2 (SEQ ID NO: 55), M3 (SEQ ID NO: 56), M4 (SEQ ID NO: 57), M5 (SEQ ID NO: 59) to M6 (SEQ ID NO: 59), where the reference peptides deviate from the peptide structure according to the invention in each case in the amino-terminal region A, carboxy-terminal region C or in the in between region B (table 3).

TABLE 3

Summary of the physico-chemical, antimicrobial and cytotoxic properties of the peptides M1 to M6. All of the values represent the arithmetic mean of the results from four independent test series.

| Peptide | Sequence[1] | Properties | | MIC [µM] | | Toxicity [µM] | | Therapeutic ratio | |
|---|---|---|---|---|---|---|---|---|---|
| | | H | µ | E. coli | S. xylosus | LD$_{50}$ | MTC | E. coli | S. xylosus |
| M1 | KRKILILIKRK (SEQ ID NO: 1) | 0.256 | 0.290 | 8 | 2 | >64 | >64 | 16 | 64 |
| M2 | KRKILILILIL (SEQ ID NO: 55) | 1.001 | 0.194 | >64 | >64 | >64 | >64 | 1 | 1 |
| M3 | ILILILILKRK (SEQ ID NO: 56) | 1.001 | 0.194 | >64 | >64 | >64 | >64 | 1 | 1 |
| M4 | KRKILILIGSG (SEQ ID NO: 57) | 0.525 | 0.249 | >64 | >64 | >64 | >64 | 1 | 1 |
| M5 | GSGILILIKRK (SEQ ID NO: 58) | 0.525 | 0.249 | >64 | >64 | >64 | >64 | 1 | 1 |
| M6 | KRKSGSGSKRK (SEQ ID NO: 59) | -0.555 | 0.090 | >64 | >64 | >64 | >64 | 1 | 1 |

[1]Sequence given as a single-letter code from the N terminus to the C terminus.

It is clear that the peptide M1 has an intensive antimicrobial effect, the MIC values being 8 µM for *E. coli* and 2 µM for *S. xylosus*. At the same time, no disadvantageous cytotoxic properties were established for the peptide M1.

It is evident from table 4 that the peptide M1 has general membrane-destroying properties above a concentration of 25 µM toward the bacteria. The outer bacteria membrane is permeabilized by the peptide of the tested concentration within 16 to 39 min, whereas the permeabilization of the inner membrane requires a concentration of 16 µM and occurs about 30 min later.

TABLE 4

Summary of the membrane-destroying properties of the peptides M1 to M6. All of the values represent the arithmetic mean of the results from four independent test series.

| Peptide | General permeabilization [µM] | | Outer membrane [min] | | | | Inner membrane [min] | | | |
|---|---|---|---|---|---|---|---|---|---|---|
| | E. coli | S. xylosus | 4 µM | 8 µM | 16 µM | 32 µM | 4 µM | 8 µM | 16 µM | 32 µM |
| M1 (SEQ ID NO: 1) | 25 | 25 | 39 | 16 | 17 | 17 | >90 | >90 | 59 | 42 |
| M2 (SEQ ID NO: 55) | >50 | >50 | >90 | >90 | 23 | 26 | >90 | >90 | >90 | >90 |
| M3 (SEQ ID NO: 56) | >50 | >50 | >90 | >90 | 42 | 33 | >90 | >90 | >90 | >90 |
| M4 (SEQ ID NO: 57) | >50 | >50 | >90 | >90 | >90 | >90 | >90 | >90 | >90 | >90 |
| M5 (SEQ ID NO: 58) | >50 | >50 | >90 | >90 | >90 | >90 | >90 | >90 | >90 | >90 |
| M6 (SEQ ID NO: 59) | >50 | >50 | >90 | >90 | >90 | >90 | >90 | >90 | >90 | >90 |

The comparison peptides M2 and M3, which each lack the region C or A, exhibit, with MIC values of >64 μM, virtually no growth inhibition of the bacteria cultures and have a therapeutic ratio of 1. For these peptides, only one permeabilization of the outer bacteria membrane is observed at the highest tested peptide concentrations. The inner membrane is not destroyed. In the case of the reference peptides M4 to M6, no antimicrobial or cytotoxic effect at all is observed.

Figure 9:
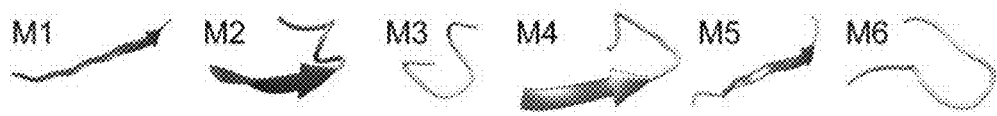
FIG. 9 shows spatial models of the peptide according to the invention M1 SEQ ID NO: 1) and the reference peptides M2 (SEQ ID NO: 55), M3 (SEQ ID NO: 56) M4 (SEQ ID NO: 57), M5 (SEQ ID NO: 58), and M6 (SEQ ID NO: 59).

A connection between the antimicrobial effect and the secondary structure of the peptides is evident from FIG. 9. The model peptide M1 forms a stretched beta strand which comprises virtually the entire peptide sequence. By contrast, the reference peptides M2, M4 and M5 form considerably shorter beta strands, with the other regions having no evident secondary structure. The reference peptides M3 and M6 are completely present as random coil.

Example 10

Execution of the Amino-Terminal Region A

The importance of the amino-terminal region A was investigated by way of example with the help of the peptides according to the invention N1 (SEQ ID NO: 5), N2 (SEQ ID NO: 3), N3 (SEQ ID NO: 4) to N4 (SEQ ID NO: 2), and also the reference peptides N5 (SEQ ID NO: 60), N6 (SEQ ID NO: 61), N7 (SEQ ID NO: 62) to N8 (SEQ ID NO: 63), the number of basic amino acids in the region A being reduced from 5 (peptide N1) to zero (peptides N5 to N8). At the same time, in the peptides N6, N7 and N8, a possible secondary influence of the ratio of the number of amino acids in the regions B and C in the absence of the region A was investigated. The investigative results are summarized in tables 5 and 6.

TABLE 5

Summary of the physico-chemical, antimicrobial and cytotoxic properties of the peptides N1 to N6 compared to M1. All of the values represent the arithmetic mean of the results from four independent test series.

| Peptide | Sequence[1] | Properties[2] | | MIC [μM] | | Toxicity [μM] | | Therapeutic ratio | |
|---|---|---|---|---|---|---|---|---|---|
| | | H | μ | E. coli | S. xylosus | $LD_{50}$ | MTC | E. coli | S. xylosus |
| N1 | KRKRKILILIKRK (SEQ ID NO: 5) | 0.063 | 0.294 | 8 | 0.5 | 36 | 32 | 4.5 | 72 |
| N2 | RKRKILILIKRK (SEQ ID NO: 3) | 0.151 | 0.236 | 8 | 2 | >64 | >64 | 16 | 64 |
| M1 | KRKILILIKRK (SEQ ID NO: 1) | 0.256 | 0.290 | 8 | 2 | >64 | >64 | 16 | 64 |
| N3 | RKILILIKRK (SEQ ID NO: 4) | 0.381 | 0.400 | 16 | 4 | >64 | >64 | 8 | 32 |
| N4 | KILILIKRK (SEQ ID NO: 2) | 0.536 | 0.381 | 32 | 16 | 58 | >64 | 1.8 | 3.6 |
| N5 | ILILIKRK (SEQ ID NO: 60) | t.s. | t.s. | 64 | 64 | >64 | >64 | 2 | 2 |
| N6 | LILIKRK (SEQ ID NO: 61) | t.s. | t.s. | >64 | >64 | >64 | >64 | 1 | 1 |
| N7 | ILIKRK (SEQ ID NO: 62) | t.s. | t.s. | >64 | >64 | >64 | >64 | 1 | 1 |
| N8 | LIKRK (SEQ ID NO: 63) | t.s. | t.s. | >64 | >64 | >64 | >64 | 1 | 1 |

[1]Sequence given as a single-letter code from the N terminus to the C terminus.
[2]t.s. indicates peptides with inadequate length for an accurate structure prediction.

It is clear that even a basic amino acid in the N-terminal region A (x=1) of the peptides according to the invention suffices to develop a strong antimicrobial effect. By way of example of this are the MIC values of 32 μM and 16 μM toward *E. coli* and *S. xylosus* of the peptide N4. At the same time, as a result of further supplementation to for example x=2, 3, 4 or 5 basic amino acids in the region A, a further reduction in the minimum inhibitory concentration, i.e. an intensification of the antimicrobial effect, can be achieved. Accordingly, the peptide N1, as an example of a peptide according to the invention with five basic amino acids in the region A, has advantageous MIC values of 8 μM and 0.5 μM. In this way, particularly advantageous peptides with a high antimicrobial activity can be provided. Only the complete elimination (x=0) of the region A in the comparison peptide N5 increases the MIC value to 64 μM, whereas the additional reduction of the region B in the comparison peptides N6 to N8 leads to MIC values of more than 64 μM.

It is evident from table 6 that the observed antimicrobial properties of the peptides correlate with the membrane-destroying properties. Accordingly, even in the presence of a basic amino acid in the amino-terminal region A above concentrations of 50 μM and 25 μM, a general membrane permeabilization in the case of *E. coli* and *S. xylosus* by the peptides according to the invention is observed. As a result of additional basic amino acids in the region A, the membrane destruction already occurs at lower peptide concentrations. For example, with the peptide N1, a general membrane destruction can already be achieved above concentrations of 25 μM and 5 μM.

These properties are also reflected in the kinetic investigations relating to the permeabilization of the outer and inner *E. coli* membrane. All of the model peptides, the amino-terminal region A of which has at least one basic amino acid, are able to destroy the outer and inner membrane, and in the case of peptides with a shortened amino-terminal region an effective permeabilization can be achieved as a result of higher peptide concentrations or longer contact periods. By contrast, in the case of reference peptides N5 to N8, no membrane destruction was established.

Figure 10:
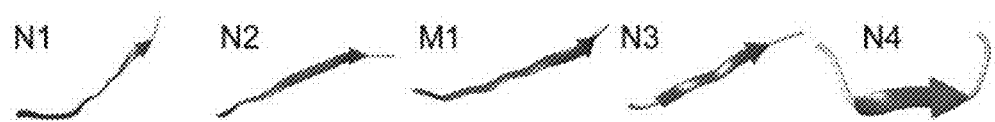
FIG. 10 shows models of the spatial structure of the peptides N1 (SEQ ID NO: 5), N2 (SEQ ID NO: 3), N3 (SEQ ID NO: 4), and N4 (SEQ ID NO: 2) according to the invention compared to peptide M1 (SEQ ID NO: 1) according to the invention.

It is again evident from FIG. 10 that there is a close relationship between the development of the antimicrobial effect of the peptides and their secondary structure. For example, the peptides N1 and N2 with in each case five or four basic amino acids in the amino-terminal region A are present just as much as the previous model peptide M1 with three basic amino acids in the amino-terminal region A is essentially present as beta strand over the entire sequence. Only the further reduction in the number of basic amino acids in the amino-terminal region A, for example to x=2 in the case of peptide N3, leads to the formation of an unstructured N-terminal region. The peptide N4 with only one basic amino acid in the region A also has a structured beta strand in the central region.

Example 11

Execution of the Carboxy-Terminal Region C

Analogously to the N-terminal region A, the influence of the number of basic amino acids in the carboxy-terminal region C was also investigated. The results are summarized by way of example by reference to the peptides according to the invention C1 (SEQ ID NO: 6), C2 (SEQ ID NO: 7), C3 (SEQ ID NO: 8) to C4 (SEQ ID NO: 9) and also the reference peptides C5 (SEQ ID NO: 64), C6 (SEQ ID NO: 65), C7 (SEQ ID NO: 66) to C8 (SEQ ID NO: 67) in table 7.

TABLE 6

Summary of the membrane-destroying properties of the peptides N1 to N6 compared with M1. All of the values represent the arithmetic mean of the results from four independent test series.

| Peptide | General permeabilization [μM] | | Outer membrane [min] | | | | Inner membrane [min] | | | |
|---|---|---|---|---|---|---|---|---|---|---|
| | *E. coli* | *S. xylosus* | 4 μM | 8 μM | 16 μM | 32 μM | 4 μM | 8 μM | 16 μM | 32 μM |
| N1 (SEQ ID NO: 5) | 25 | 5 | 21 | 14 | 12 | 11 | >90 | >90 | 38 | 32 |
| N2 (SEQ ID NO: 3) | 25 | 5 | 20 | 13 | 12 | 12 | >90 | >90 | 40 | 32 |
| M1 (SEQ ID NO: 1) | 25 | 25 | 39 | 16 | 17 | 17 | >90 | >90 | 59 | 42 |
| N3 (SEQ ID NO: 4) | 25 | 25 | 41 | 40 | 21 | 13 | >90 | >90 | >90 | 56 |
| N4 (SEQ ID NO: 2) | 50 | 25 | 54 | 49 | 31 | 17 | >90 | >90 | >90 | >90 |
| N5 (SEQ ID NO: 60) | >50 | >50 | >90 | >90 | 48 | 37 | >90 | >90 | >90 | >90 |
| N6 (SEQ ID NO: 61) | >50 | >50 | >90 | >90 | >90 | >90 | >90 | >90 | >90 | >90 |
| N7 (SEQ ID NO: 62) | >50 | >50 | >90 | >90 | >90 | >90 | >90 | >90 | >90 | >90 |
| N8 (SEQ ID NO: 63) | >50 | >50 | >90 | >90 | >90 | >90 | >90 | >90 | >90 | >90 |

TABLE 7

Summary of the physico-chemical, antimicrobial and cytotoxic properties of the peptides C1 to C8 compared to M1. All of the values represent the arithmetic mean of the results from four independent test series.

| Peptide | Sequence[1] | Properties[2] H | μ | MIC [μM] E. coli | E. xylosus | Toxicity [μM] LD$_{50}$ | MTC | Therapeutic ratio E. coli | S. xylosus |
|---|---|---|---|---|---|---|---|---|---|
| C1 | KRKILILIKRKRK (SEQ ID NO: 6) | 0.063 | 0.294 | 16 | 1 | 61 | >64 | 3.8 | 61 |
| C2 | KRKILILIKRKR (SEQ ID NO: 7) | 0.151 | 0.236 | 16 | 2 | >64 | >64 | 8 | 64 |
| M1 | KRKILILIKRK (SEQ ID NO: 1) | 0.256 | 0.290 | 8 | 2 | >64 | >64 | 16 | 64 |
| C3 | KRKILILIKR (SEQ ID NO: 8) | 0.381 | 0.400 | 16 | 8 | >64 | >64 | 8 | 16 |
| C4 | KRKILILIK (SEQ ID NO: 9) | 0.536 | 0.381 | 32 | 8 | >64 | >64 | 4 | 16 |
| C5 | KRKILILI (SEQ ID NO: 64) | t.s. | t.s. | >64 | >64 | >64 | >64 | 1 | 1 |
| C6 | KRKILIL (SEQ ID NO: 65) | t.s. | t.s. | >64 | >64 | >64 | >64 | 1 | 1 |
| C7 | KRKILI (SEQ ID NO: 66) | t.s. | t.s. | >64 | >64 | >64 | >64 | 1 | 1 |
| C8 | KRKIL (SEQ ID NO: 67) | t.s. | t.s. | >64 | >64 | >64 | >64 | 1 | 1 |

[1]Sequence given as a single-letter code from the N terminus to the C terminus.
[2]t.s. indicates peptides with an inadequate length of an accurate structure prediction.

The results correspond essentially to those which were observed analogously for the N-terminal region. Even above one basic amino acid in the carboxy-terminal region C (z=1), a significant antimicrobial effect of the peptides is achieved. By way of example here are the MIC values of 32 μM toward E. coli and 8 μM toward S. xylosus of the model peptide C4. As a result of expanding the C-terminal region to, for example, two, three, four, or five basic amino acids, it is possible to further increase the antimicrobial effect. For example, the peptide C1 with five basic amino acids in the region C has an MIC of 16 μM and 1 μM. For the reference peptides without basic amino acid in the C-terminal region, no antimicrobial activity could be detected, meaning that the therapeutic ratio was just 1.

TABLE 8

Summary of the membrane-destroying properties of the peptides C1 to C8 compared to M1. All of the values represent the arithmetic mean of the results from four independent test series.

| Peptide | General permeabilization [μM] E. coli | S. xylosus | Outer membrane [min] 4 μM | 8 μM | 16 μM | 32 μM | Inner membrane [min] 4 μM | 8 μM | 16 μM | 32 μM |
|---|---|---|---|---|---|---|---|---|---|---|
| C1 (SEQ ID NO: 6) | 25 | 25 | 38 | 30 | 23 | 13 | >90 | >90 | 62 | 45 |
| C2 (SEQ ID NO: 7) | 25 | 25 | 40 | 27 | 22 | 16 | >90 | >90 | 64 | 47 |
| M1 (SEQ ID NO: 1) | 25 | 25 | 39 | 16 | 17 | 17 | >90 | >90 | 59 | 42 |

TABLE 8-continued

Summary of the membrane-destroying properties of the peptides C1 to C8 compared to M1. All of the values represent the arithmetic mean of the results from four independent test series.

| Peptide | General permeabilization [µM] | | Outer membrane [min] | | | | Inner membrane [min] | | | |
|---|---|---|---|---|---|---|---|---|---|---|
| | *E. coli* | *S. xylosus* | 4 µM | 8 µM | 16 µM | 32 µM | 4 µM | 8 µM | 16 µM | 32 µM |
| C3 (SEQ ID NO: 8) | 50 | 25 | 42 | 30 | 21 | 19 | >90 | >90 | 50 | 45 |
| C4 (SEQ ID NO: 9) | 50 | 25 | 41 | 37 | 25 | 12 | >90 | >90 | 53 | 42 |
| C5 (SEQ ID NO: 64) | >50 | >50 | >90 | >90 | 26 | 23 | >90 | >90 | >90 | >90 |
| C6 (SEQ ID NO: 65) | >50 | >50 | >90 | >90 | >90 | >90 | >90 | >90 | >90 | >90 |
| C7 (SEQ ID NO: 66) | >50 | >50 | >90 | >90 | >90 | >90 | >90 | >90 | >90 | >90 |
| C8 (SEQ ID NO: 67) | >50 | >50 | >90 | >90 | >90 | >90 | >90 | >90 | >90 | >90 |

Figure 11:
FIG. 11 shows models of the spatial structure of the peptides C1 (SEQ ID NO: 6), C2 (SEQ ID NO: 7), C3 (SEQ ID NO: 8), and C4 (SEQ ID NO: 9) according to the invention compared to peptide M1 (SEQ ID NO: 1) according to the invention.

Such a correspondence can also be found in the results of the kinetic investigations relating to membrane permeabilization (table 8) and in the investigation of the secondary structures, which exhibit stretched beta strands for the peptides C1 and C2 which comprise virtually the entire sequence of the peptide (FIG. 11). By contrast, the peptide C3, with only two basic amino acids on the C terminus, has a shortened beta strand motif in combination with two unstructured regions on the termini. The peptide C4 with a basic amino acid on the C terminus also has a shortened beta strand on the N terminus, whereas the region adjacent to it is present as random coil.

Example 12

Execution of the Central Region B

By way of example, the influence of the number of hydrophobic or nonpolar amino acids in the central region B of the peptide was systematically investigated by reference to the peptides according to the invention H1 (SEQ ID NO: 10), H2 (SEQ ID NO: 11) to H3 (SEQ ID NO: 12), and also the reference peptides H4 (SEQ ID NO: 68), H5 (SEQ ID NO: 69), H6 (SEQ ID NO: 70), H7 (SEQ ID NO: 71) to H8 (SEQ ID NO: 72) (table 9).

TABLE 9

Summary of the physico-chemical, antimicrobial and cytotoxic properties of the peptides H1 to H8 compared to M1. All of the values represent the arithmetic mean of the results from four independent test series.

| | | Properties[2] | | MIC [µM] | | Toxicity [µM] | | Therapeutic ratio | |
|---|---|---|---|---|---|---|---|---|---|
| Peptide | Sequence[1] | H | µ | *E. coli* | *S. xylosus* | LD$_{50}$ | MTC | *E. coli* | *S. xylosus* |
| H1 | KRKILILILIKRK (SEQ ID NO: 10) | 0.486 | 0.054 | 8 | 1 | >64 | >64 | 16 | 128 |
| M1 | KRKILILIKRK (SEQ ID NO: 1) | 0.256 | 0.290 | 8 | 2 | >64 | >64 | 16 | 64 |
| H2 | KRKLILIKRK (SEQ ID NO: 11) | 0.102 | 0.209 | >64 | 16 | >64 | >64 | 1 | 8 |
| H3 | KRKILIKRK (SEQ ID NO: 12) | -0.008 | 0.045 | >64 | 64 | >64 | >64 | 1 | 2 |
| H4 | KRKLIKRK (SEQ ID NO: 68) | t.s. | t.s. | >64 | >64 | >64 | >64 | 1 | 1 |
| H5 | KRKIKRK (SEQ ID NO: 69) | t.s. | t.s. | >64 | >64 | >64 | >64 | 1 | 1 |

TABLE 9-continued

Summary of the physico-chemical, antimicrobial and cytotoxic properties of the peptides H1 to H8 compared to M1. All of the values represent the arithmetic mean of the results from four independent test series.

| Peptide | Sequence[1] | Properties[2] H | μ | MIC [μM] E. coli | S. xylosus | Toxicity [μM] LD$_{50}$ | MTC | Therapeutic ratio E. coli | S. xylosus |
|---|---|---|---|---|---|---|---|---|---|
| H6 | KRKKRK (SEQ ID NO: 70) | t.s. | t.s. | >64 | 16 | >64 | >64 | 1 | 8 |
| H7 | KRKGKRK (SEQ ID NO: 71) | t.s. | t.s. | >64 | 64 | >64 | >64 | 1 | 2 |
| H8 | KRKGSGKRK (SEQ ID NO: 72) | −0.669 | 0.078 | >64 | >64 | >64 | >64 | 1 | 1 |

[1]Sequence given as a single-letter code from the N terminus to the C terminus.
[2]t.s. indicates peptides with an inadequate length of an accurate structure prediction.

Already above three continuous hydrophobic and/or nonpolar amino acids in the region B, the peptides are equipped with advantageous antimicrobial properties. For example, the peptide H3 has an MIC of 64 μM against *S. xylosus*. As a result of adding further hydrophobic and/or nonpolar amino acids, a higher antimicrobial activity can be achieved. For example, the MIC of the peptide H2 toward *S. xylosus* is already 16 μM, whereas the peptide H1 with seven hydrophobic amino acids is equipped with particularly marked antimicrobial properties, which are reflected in MIC values of 8 μM against *E. coli* and 1 μM against *S. xylosus*.

For the comparison peptides H4 to H8 with two or fewer hydrophobic amino acids in the central region, no antimicrobial activities corresponding to the peptides according to the invention could be detected.

The substitution of the hydrophobic and/or nonpolar amino acids in the central region by neutral amino acids also did not lead to a reestablishment of the antimicrobial activity. A corresponding tendency was also observed in the case of the kinetic investigations relating to membrane permeabilization in general and the permeabilization of the outer and inner membranes specifically (table 10).

TABLE 10

Summary of the membrane-destroying properties of the peptides H1 to H8 compared with M1. All of the values represent the arithmetic mean of the results from four independent test series.

| Peptide | General permeabilization [μM] | | Outer membrane [min] | | | | Inner membrane [min] | | | |
|---|---|---|---|---|---|---|---|---|---|---|
| | E. coli | S. xylosus | 4 μM | 8 μM | 16 μM | 32 μM | 4 μM | 8 μM | 16 μM | 32 μM |
| H1 (SEQ ID NO: 10) | 50 | 5 | 26 | 20 | 19 | 17 | >90 | 37 | 35 | 33 |
| M1 (SEQ ID NO: 1) | 25 | 25 | 39 | 16 | 17 | 17 | >90 | >90 | 59 | 42 |
| H2 (SEQ ID NO: 11) | >50 | 25 | >90 | >90 | >90 | >90 | >90 | >90 | >90 | >90 |
| H3 (SEQ ID NO: 12) | >50 | 50 | >90 | >90 | >90 | >90 | >90 | >90 | >90 | >90 |
| H4 (SEQ ID NO: 68) | >50 | >50 | >90 | >90 | >90 | >90 | >90 | >90 | >90 | >90 |
| H5 (SEQ ID NO: 69) | >50 | >50 | >90 | >90 | >90 | >90 | >90 | >90 | >90 | >90 |
| H6 (SEQ ID NO: 70) | >50 | >50 | >90 | >90 | >90 | >90 | >90 | >90 | >90 | >90 |
| H7 (SEQ ID NO: 71) | >50 | >50 | >90 | >90 | >90 | >90 | >90 | >90 | >90 | >90 |
| H8 (SEQ ID NO: 72) | >50 | >50 | >90 | >90 | >90 | >90 | >90 | >90 | >90 | >90 |

Figure 12:
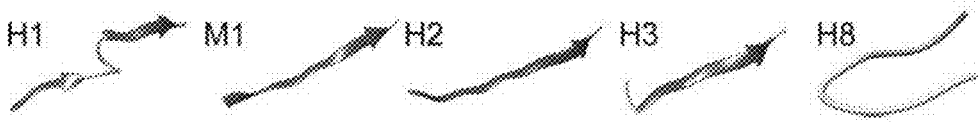
FIG. 12 shows models of the spatial structure of the peptides H1 (SEQ ID NO: 10), H2 (SEQ ID NO: 11), and H3 (SEQ ID NO: 12) according to the invention and the reference peptide H8 (SEQ ID NO: 72) compared to the peptide M1 (SEQ ID NO: 1) according to the invention.

The secondary structure of the peptide H1 is characterized by in each case one beta strand in the C- and N-terminal region and an unstructured region in between, whereas the peptide H2 forms a single beta strand over almost the entire sequence (FIG. 12). The peptide H3 has a stretched beta strand in the central region which is flanked only by two short unstructured regions. In contrast to this, the peptide H8, which although it has in each case three basic amino acids in the C-terminal region and N-terminal region, has only neutral amino acids in the central region, is present completely as random coil.

Example 13
Execution as Regards the Arrangement of Hydrophobic and/or Nonpolar Amino Acids and Basic Amino Acids In the next step, the role of the arrangement of hydrophobic and basic amino acids within the peptide sequence was investigated. The results are shown in table 11 by way of example of the peptides according to the invention A1 (SEQ ID NO: 13) and A2 (SEQ ID NO: 14), and also the reference peptides A3 (SEQ ID NO: 73), A4 (SEQ ID NO: 74) to A5 (SEQ ID NO: 15). In these peptides, the hydrophobic amino acids have been shifted stepwise from the central region of the sequence into the amino- or carboxy-terminal regions and the basic amino acids have been accordingly shifted from the terminal regions into the central region. In this way, peptides of identical length and hydrophobicity result, but with different hydrophobic moments and primary sequences.

TABLE 11

Summary of the physico-chemical, antimicrobial and cytotoxic properties of the peptides A1 to A5. All of the values represent the arithmetic mean of the results from four independent test series.

| Peptide | Sequence[1] | Properties H | μ | MIC [μM] E. coli | MIC [μM] S. xylosus | Toxicity [μM] $LD_{50}$ | Toxicity [μM] MTC | Therapeutic ratio E. coli | Therapeutic ratio S. xylosus |
|---|---|---|---|---|---|---|---|---|---|
| A1 | RKRKLILILIKRKR (SEQ ID NO: 13) | 0.179 | 0.191 | 8 | 0.5 | >64 | >64 | 16 | 256 |
| A2 | KRKLILKRILIKRK (SEQ ID NO: 14) | 0.179 | 0.054 | 16 | 8 | >64 | >64 | 8 | 16 |
| A3 | RKLILKRKRILIKR (SEQ ID NO: 73) | 0.179 | 0.283 | 16 | 8 | >64 | >64 | 8 | 16 |
| A4 | KLILKRKRKRILIK (SEQ ID NO: 74) | 0.179 | 0.034 | 32 | 16 | >64 | >64 | 4 | 8 |
| A5 | LILKRKRKRKRILI (SEQ ID NO: 75) | 0.179 | 0.221 | >64 | >64 | >64 | >64 | 1 | 1 |

[1]Sequence stated as a single-letter code from the N terminus to the C terminus.

It is evident that the interruption of the sequence of hydrophobic or nonpolar amino acids in the central region B by one or more other amino acids, for example basic amino acids, also ensures the provision of antimicrobially effective peptides so long as B has at least 65% hydrophobic/nonpolar amino acids and a direct sequence of at least three hydrophobic/nonpolar amino acids. The interruption of the structural motif according to the invention by arrangement of only 60% hydrophobic and/or nonpolar amino acids in the region B, e.g. peptide A3, or 40% hydrophobic and/or nonpolar amino acids in the region B, e.g. peptide A4, results in a deterioration of the MIC values toward E. coli and S. xylosus. The complete replacement of the hydrophobic and basic amino acids in the peptide A5 leads to a complete loss of the antimicrobial properties. Corresponding trends are also reflected in the kinetic properties with regard to the permeabilization of the outer and inner bacteria membrane of the peptides according to the invention (table 12).

TABLE 12

Summary of the membrane-destroying properties of the peptides A1 to A5. All the values represent the arithmetic mean of the results from four independent test series.

| Peptide | Permeabilization [μM] | | Outer membrane [min] | | | | Inner membrane [min] | | | |
|---|---|---|---|---|---|---|---|---|---|---|
| | E. coli | S. xylosus | 4 μM | 8 μM | 16 μM | 32 μM | 4 μM | 8 μM | 16 μM | 32 μM |
| A1 (SEQ ID NO: 13) | 25 | 5 | 26 | 21 | 17 | 16 | >90 | 42 | 40 | 35 |
| A2 (SEQ ID NO: 14) | >50 | 25 | >90 | >90 | 21 | 16 | >90 | >90 | 60 | 80 |
| A3 (SEQ ID NO: 73) | >50 | 50 | >90 | >90 | >90 | 17 | >90 | >90 | >90 | 72 |
| A4 (SEQ ID NO: 74) | >50 | >50 | >90 | >90 | >90 | >90 | >90 | >90 | >90 | >90 |
| A5 (SEQ ID NO: 75) | >50 | >50 | >90 | >90 | >90 | >90 | >90 | >90 | >90 | >90 |

Figure 13:
FIG. 13 shows models of the spatial structure of the peptides A1 (SEQ ID NO: 13) and A2 (SEQ ID NO: 14) according to the invention and also the reference peptides A3 (SEQ ID NO: 73), A4 (SEQ ID NO: 74), and A5 (SEQ ID NO: 75).

The secondary structure of the peptide A1 is largely characterized by beta strands whereas the interruption of the hydrophobic central region with two basic amino acids in the case of peptide A2 leads to a structural change ranging to an alpha-helical motif (FIG. 13).

Example 14

Execution of the Amino Acid Composition

For the investigation of the influence of individual amino acids on the antimicrobial and cytotoxic properties of the antimicrobial peptides, a model peptide motif with in each case three basic amino acids in the regions A and C, and six hydrophobic/nonpolar amino acids in the central region B was used. On the basis of this motif, lysine and arginine were listed as exemplary basic amino acids, and isoleucine, leucine, phenylalanine and valine were listed as exemplary hydrophobic/nonpolar amino acids in a combinatorial manner, and the antimicrobial properties of the corresponding peptides according to the invention S1 (SEQ ID NO: 15), S2 (SEQ ID NO: 16), S3 (SEQ ID NO: 17), S4 (SEQ ID NO: 18), S5 (SEQ ID NO: 19), S6 (SEQ ID NO: 20), S7 (SEQ ID NO: 21) and S8 (SEQ ID NO: 22) (table 13).

TABLE 13

Summary of the physico-chemical, antimicrobial and cytotoxic properties of the peptides S1 to S8. All of the values represent the arithmetic mean of the results from four independent test series.

| Peptide | Sequence[1] | Properties | | MIC [μM] | | Toxicity [μM] | | Therapeutic ratio | |
|---|---|---|---|---|---|---|---|---|---|
| | | H | μ | E. coli | S. xylosus | $LD_{50}$ | MTC | E. coli | S. xylosus |
| S1 | RRRIIIIIRRR (SEQ ID NO: 15) | 0.267 | 0.293 | 8 | 2 | >64 | 64 | (16) | (64) |
| S2 | KKKIIIIIKKK (SEQ ID NO: 16) | 0.278 | 0.291 | 8 | 0.5 | >64 | >64 | 16 | 256 |
| S3 | RRRLLLLLRRR (SEQ ID NO: 17) | 0.222 | 0.281 | 8 | 1 | >64 | 64 | (16) | (128) |
| S4 | KKKLLLLLKKK (SEQ ID NO: 18) | 0.233 | 0.280 | 16 | 8 | >64 | >64 | 4 | 8 |
| S5 | RRRVVVVVRRR (SEQ ID NO: 19) | 0.004 | 0.228 | 32 | 2 | >64 | >64 | 4 | 64 |
| S6 | KKKVVVVVKKK (SEQ ID NO: 20) | 0.015 | 0.226 | 64 | 8 | >64 | >64 | 2 | 16 |

TABLE 13-continued

Summary of the physico-chemical, antimicrobial and cytotoxic properties of the peptides S1 to S8. All of the values represent the arithmetic mean of the results from four independent test series.

| Peptide | Sequence[1] | Properties | | MIC [μM] | | Toxicity [μM] | | Therapeutic ratio | |
|---|---|---|---|---|---|---|---|---|---|
| | | H | μ | E. coli | S. xylosus | LD$_{50}$ | MTC | E. coli | S. xylosus |
| S7 | RRRFFFFFRRR (SEQ ID NO: 21) | 0.263 | 0.291 | 4 | 0.5 | >64 | 32 | (32) | (256) |
| S8 | KKKFFFFFKKK (SEQ ID NO: 22) | 0.274 | 0.290 | 16 | 4 | >64 | >64 | 8 | 32 |

[1]Sequence given as a single-letter code from the N terminus to the C terminus.
[2]Values in parentheses mean that a MTC was established, but no LD$_{50}$.

In principle, an advantageous antimicrobial effect was achieved with all of the peptides S1 to S8, the MIC values being between 4 μM and 64 μM for E. coli and 0.5 μM to 8 μM for S. xylosus. As regards the basic amino acids, the use of arginine as compared with lysine led to a stronger antimicrobial effect, which is reflected in the MIC values in table 13 and the results of the kinetic investigation in table 14. At the same time, the peptides S1, S3 and S7 with arginine as basic amino acid, however, also have growth-inhibiting properties toward the eukaryotic cell line U937. Here in turn is found an advantage of the lysine-containing peptides S2, S4, S6 and S8, which have no corresponding cytotoxic properties.

For example, therefore, those antimicrobial peptides which are listed with an increased fraction of lysine as basic amino acid in the regions A and C can, on account of their high selectivity toward bacterial membranes, be used particularly advantageously in the medical-therapeutic sector since, for example, human cells are not damaged. On account of their strong antimicrobial properties, peptides with an increased fraction of arginine as basic amino acid in the regions A and C are particularly suitable for ex vivo applications, for example as constituent of antimicrobial compositions and coatings for antifouling.

With regard to the central region B, particularly advantageous antimicrobial properties are achieved with the amino acids isoleucine, leucine and phenylalanine.

TABLE 14

Summary of the membrane-destroying properties of the peptides S1 to S8. All of the values represent the arithmetic mean of the results from four independent test series.

| Peptide | General permeabilization [μM] | | Outer membrane [min] | | | | Inner membrane [min] | | | |
|---|---|---|---|---|---|---|---|---|---|---|
| | E. coli | S. xylosus | 4 μM | 8 μM | 16 μM | 32 μM | 4 μM | 8 μM | 16 μM | 32 μM |
| S1 (SEQ ID NO: 15) | 25 | 25 | 25 | 24 | 22 | 19 | >90 | 63 | 61 | 56 |
| S2 (SEQ ID NO: 16) | 25 | 5 | 26 | 23 | 21 | 21 | >90 | 62 | 58 | 51 |
| S3 (SEQ ID NO: 17) | 50 | 25 | >90 | 32 | 22 | 15 | >90 | >90 | >90 | 83 |
| S4 (SEQ ID NO: 18) | 50 | 50 | >90 | >90 | >90 | 24 | >90 | >90 | >90 | 91 |
| S5 (SEQ ID NO: 19) | 50 | 25 | >90 | >90 | >90 | 19 | >90 | >90 | >90 | >90 |
| S6 (SEQ ID NO: 20) | >50 | >50 | >90 | >90 | >90 | 31 | >90 | >90 | >90 | >90 |
| S7 (SEQ ID NO: 21) | 25 | 25 | >90 | 14 | 13 | 9 | >90 | 39 | 37 | 34 |
| S8 (SEQ ID NO: 22) | 50 | 50 | >90 | >90 | >90 | 20 | >90 | >90 | >90 | 64 |

Example 15

Execution with Acidic Amino Acids

The structural motif according to the invention was further analyzed as regards the embodiment possibilities with acidic amino acids, i.e. negatively charged residues. Table 14 shows representative results for a basic structure with five basic amino acids in each case in the amino-terminal region A and carboxy-terminal region C, and also five hydrophobic/nonpolar amino acids in the central region B. Exemplary variations of this basic structure were carried out by replacing basic amino acids in the carboxy-terminal region stepwise by acidic amino acids, for example aspartic acid. In this way, the peptides according to the invention D4 (SEQ ID NO: 23), D5 (SEQ ID NO: 24), D6 (SEQ ID NO: 25) and D7 (SEQ ID NO: 26), and also the reference peptides D1 (SEQ ID NO: 76), D2 (SEQ ID NO: 77) and D3 (SEQ ID NO: 78), and D8 (SEQ ID NO: 79) were generated.

TABLE 15

Summary of the physico-chemical, antimicrobial and cytotoxic properties of the peptides D1 to D8. All of the values represent the arithmetic mean of the results from four independent test series.

| Peptide | Sequence[1] | Properties H | μ | MIC [μM] E. coli | MIC [μM] S. xylosus | Toxicity [μM] LD$_{50}$ | Toxicity [μM] MTC | Therapeutic ratio E. coli | Therapeutic ratio S. xylosus |
|---|---|---|---|---|---|---|---|---|---|
| D1 | KKKKKIIIIIDDDDD (SEQ ID NO: 76) | 0.013 | 0.258 | >64 | >64 | >64 | >64 | 1 | 1 |
| D2 | KKKKKIIIIIKDDDD (SEQ ID NO: 77) | -0.001 | 0.265 | >64 | >64 | >64 | >64 | 1 | 1 |
| D3 | KKKKKIIIIIKKKDD (SEQ ID NO: 78) | -0.031 | 0.265 | >64 | 32 | >64 | >64 | 1 | 4 |
| D4 | KKKKKIIIIIKKKKD (SEQ ID NO: 23) | -0.045 | 0.258 | 32 | 16 | >64 | >64 | 4 | 8 |
| D5 | KKKKKIIIIIKKKKK (SEQ ID NO: 24) | -0.060 | 0.271 | 16 | 2 | >64 | >64 | 8 | 64 |
| D6 | KKKKKIIIIIDKKKK (SEQ ID NO: 25) | -0.045 | 0.264 | 32 | 16 | >64 | >64 | 4 | 8 |
| D7 | KKKKKIIIIIDDDKK (SEQ ID NO: 26) | -0.016 | 0.264 | >64 | >64 | >64 | >64 | 1 | 1 |
| D8 | KKKKKIIIIIDDDDK (SEQ ID NO: 79) | -0.001 | 0.271 | >64 | >64 | >64 | >64 | 1 | 1 |

[1]Sequence given as a single-letter code from the N terminus to the C terminus.

The peptide D5 with the aforementioned basic structure has a high antimicrobial activity and at the same time no cytotoxic properties. The MIC values are 16 μM for *E. coli* and 2 μM for *S. xylosus*. The replacement of a basic amino acid with an acidic amino acid in the transition of the central region B into the carboxy-terminal region C or on the carboxy terminus of C results in an advantageous, albeit slightly reduced antimicrobial activity with MIC values of 32 μM or 16 μM (compare peptides D6 and D4). The further replacement of basic amino acids with acidic amino acids leads to a reduction in the antimicrobial effectiveness, meaning that for a fraction of less than 60% of basic amino acids in the carboxy-terminal region C, antimicrobial activity can virtually no longer be detected.

TABLE 16

Summary of the membrane-destroying properties of the peptides D1 to D8. All of the values represent the arithmetic mean of the results from four independent test series.

| Peptide | General permeabilization [μM] E. coli | General permeabilization [μM] S. xylosus | Outer membrane [min] 4 μM | Outer membrane [min] 8 μM | Outer membrane [min] 16 μM | Outer membrane [min] 32 μM | Inner membrane [min] 4 μM | Inner membrane [min] 8 μM | Inner membrane [min] 16 μM | Inner membrane [min] 32 μM |
|---|---|---|---|---|---|---|---|---|---|---|
| D1 (SEQ ID NO: 76) | >50 | >50 | >90 | >90 | >90 | >90 | >90 | >90 | >90 | >90 |

TABLE 16-continued

Summary of the membrane-destroying properties of the peptides D1 to D8. All of the values represent the arithmetic mean of the results from four independent test series.

| Peptide | General permeabilization [µM] | | Outer membrane [min] | | | | Inner membrane [min] | | | |
|---|---|---|---|---|---|---|---|---|---|---|
| | E. coli | S. xylosus | 4 µM | 8 µM | 16 µM | 32 µM | 4 µM | 8 µM | 16 µM | 32 µM |
| D2 (SEQ ID NO: 77) | >50 | >50 | >90 | >90 | >90 | >90 | >90 | >90 | >90 | >90 |
| D3 (SEQ ID NO: 78) | >50 | >50 | >90 | >90 | >90 | >90 | >90 | >90 | >90 | >90 |
| D4 (SEQ ID NO: 23) | 50 | 25 | >90 | >90 | >90 | >90 | >90 | >90 | >90 | >90 |
| D5 (SEQ ID NO: 24) | 25 | 5 | 32 | 29 | 28 | 26 | >90 | 68 | 66 | 59 |
| D6 (SEQ ID NO: 25) | >50 | 25 | >90 | >90 | >90 | >90 | >90 | >90 | >90 | >90 |
| D7 (SEQ ID NO: 26) | >50 | >50 | >90 | >90 | >90 | >90 | >90 | >90 | >90 | >90 |
| D8 (SEQ ID NO: 79) | >50 | >50 | >90 | >90 | >90 | >90 | >90 | >90 | >90 | >90 |

Figure 14:
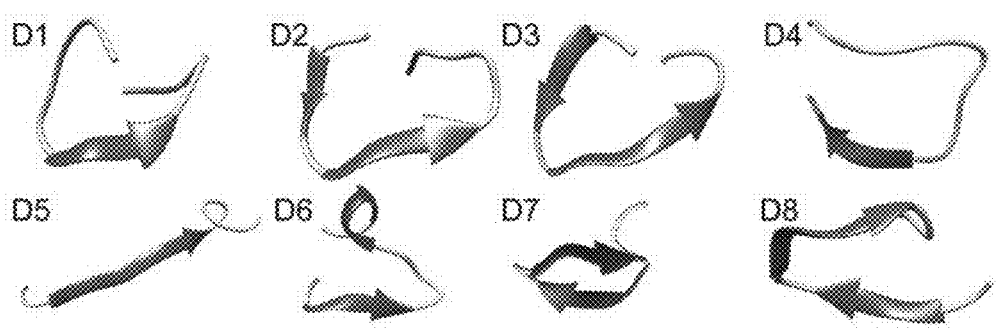
FIG. 14 shows models of the spatial structure of the reference peptides D1 (SEQ ID NO: 76), D2 (SEQ ID NO: 77), D3 (SEQ ID NO: 78) and D8 (SEQ ID NO: 79), and also of the peptides D4 (SEQ ID NO: 23), D5 (SEQ ID NO: 24), D6 (SEQ ID NO: 25), and D7 (SEQ ID NO: 26) according to the invention.

It can in turn be deduced from FIG. 14 that the decrease in the antimicrobial activity compared to the peptide D5 correlates structurally with a reduction or interruption of the stretched beta strand.

Example 16

Treatment of Bacterially Contaminated Cell Culture

The medically therapeutic potential of the peptides according to the invention was investigated with the help of mixed culture experiments as described in example 7. Shown here by way of example in table 17 and table 18 are the results of the investigation of the peptide O1 according to the invention (SEQ ID NO: 27) with a central region B of six hydrophobic/nonpolar amino acids and the flanking regions A and C with in each case three basic amino acids. Furthermore, the peptide O1' was investigated, which has the same sequence but where the carboxy terminus was formed as amide (—$CONH_2$) instead of as free acid (—COOH).

TABLE 17

Summary of the physico-chemical, antimicrobial and cytotoxic properties of the peptide O1 and the antimicrobial properties of the peptide O1'. All of the values represent the arithmetic mean of the results from four independent test series.

| Peptide | Sequence[1] | Properties | | MIC [µM] | | Toxicity [µM] | | Therapeutic ratio | |
|---|---|---|---|---|---|---|---|---|---|
| | | H | µ | E. coli | S. xylosus | $LD_{50}$ | MTC | E. coli | S. xylosus |
| O1 | KKKIIIIIIKKK (SEQ ID NO: 27) | 0.405 | 0.170 | 8 | 0.5 | >64 | >64 | 16 | 256 |
| O1' | KKKIIIIIIKKK-CONH2 (SEQ ID NO: 27) | not det. | not det. | 4 | 0.25 | not det. | not det. | not det. | not det. |

[1]Sequence given as a single-letter code from the N terminus to the C terminus.

A high antimicrobial activity with MIC values between 8 µM and 0.5 µM was established for the peptide O1. Surprisingly, the antimicrobial activity of the peptide O1 could again be doubled as a result of the amidation of the carboxy terminus, represented by O1', which manifested itself in a further reduction in the MIC values to 4 µM and 0.25 µM.

The peptide O1 displayed a marked membrane destruction with regard to *E. coli* and *S. xylosus* at peptide concentrations of 25 µM and 5 µM, respectively. In the kinetic investigations, a permeabilization of the outer and inner membrane of *E. coli* ML-35p could already be established above a concentration of 4 µM.

TABLE 18

Summary of the membrane-destroying properties of the peptide O1. All of the values represent the arithmetic mean of the results from four independent test series.

| Peptide | General permeablization [µM] | | Outer membrane [min] | | | | Inner membrane [min] | | | |
|---|---|---|---|---|---|---|---|---|---|---|
| | *E. coli* | *S. xylosus* | 4 µM | 8 µM | 16 µM | 32 µM | 4 µM | 8 µM | 16 µM | 32 µM |
| O1 (SEQ ID NO: 27) | 25 | 5 | 23 | 21 | 19 | 17 | 41 | 39 | 39 | 39 |

At the same time, no cytotoxic properties toward the eukaryotic cell line U937 could be established, meaning that particularly advantageous therapeutic ratios of 16 and 256 resulted.

Figure 15:
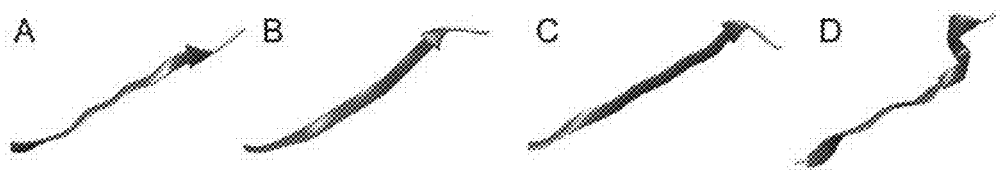
FIG. 15 shows models of the spatial structure of the peptide O1 (SEQ ID NO: 27) according to the invention in an aqueous environment according to the prediction using the PEP-fold webserver (A), and also models of the spatial structure of the peptide O1 (SEQ ID NO: 27) in an aqueous (B) and a hydrophobic (C) medium, and also in vacuo (D) according to the prediction with the PEPstr peptide tertiary structure prediction webserver.

The secondary structure of the peptide confirms the marked beta-strand structure of the peptides according to the invention in connection with the antimicrobial effectiveness (FIG. 15).

Figure 7:
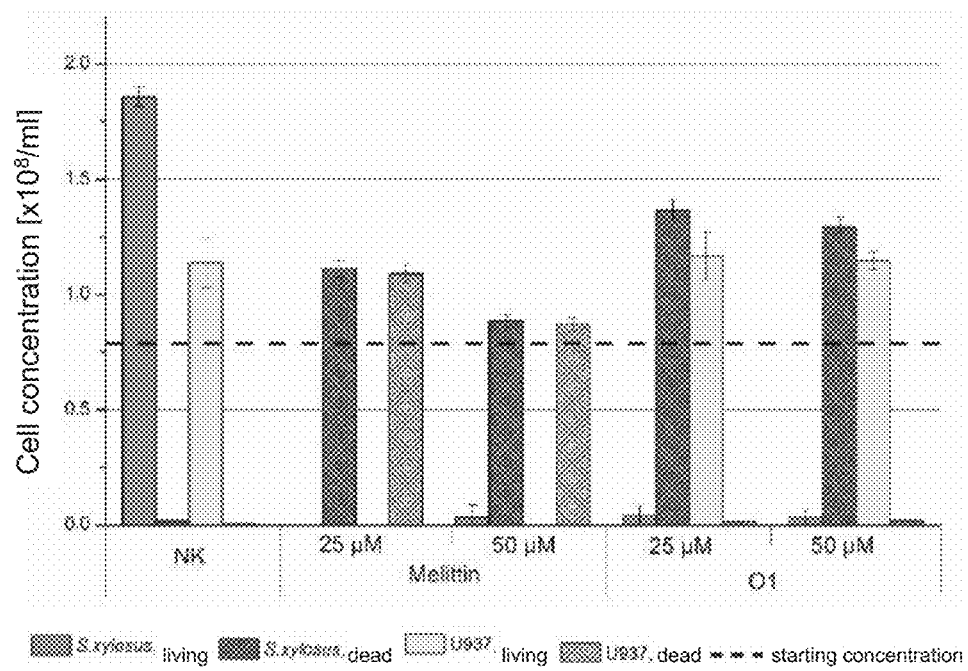
FIG. 7 shows representative results of the concentration- and peptide-dependent membrane permeabilization of *S. xylosus* and of the human cell line U937 in a mixed culture experiment. In the bar graph, the cell concentration is plotted broken down according to living and dead cells over the concentration of the natural reference peptide melittin (SEQ ID NO: 50) and the peptide O1 (SEQ ID NO: 27) according to the invention, and also the negative control as reference parameter.

This highly selective effect toward bacterial cell membranes is confirmed by the mixed culture experiments (FIG. 7). The bar graph shows, by way of example, the ratios of living and dead bacteria cells (*S. xylosus*) and eukaryotic U937 cells in the mixed culture for the negative control (NC) and also following the addition of 25 and 50 µM of melittin or peptide O1. The control experiments (NC) show essentially only living bacteria cells and eukaryotic U937 cells. Although the natural antimicrobial reference peptide melittin leads to the comprehensive killing of bacteria cells in both of the tested concentrations, the melittin, however, at the same also destroys all of the eukaryotic U937 cells. In contrast to this, it is found that a peptide according to the invention leads, already above a concentration of 25 µM, to a virtually complete killing of the *S. xylosus* cells, whereas the eukaryotic U937 cells remain uninfluenced by the treatment with the peptide. Consequently, it was able to be shown that the antimicrobial property of the peptides according to the invention has a highly selective effect toward bacteria cells and does not damage eukaryotic cells. This gives rise to particular advantages for the medical therapeutic use of the peptides according to the invention. For example, in contrast to conventional antimicrobial peptides, cytotoxic side effects can be effectively avoided in the case of an antibiosis, which contributes to improved tolerability and higher patient safety.

The invention is not limited by the description by reference to the working examples. Instead, the invention encompasses any new feature and also any combination of features, which includes in particular any combination of features in the patent claims, even if this feature or this combination is per se not explicitly stated in the patent claims or working examples.

LITERATURE (Ahmad et al. 2009) Ahmad, A., Azmi, S., Srivastava, R. M., Srivastava, S., Pandey, B. K., Saxena, R., Bajpai, V. K., and Ghosh, J. K. (2009) Design of nontoxic analogues of cathelicidin-derived bovine antimicrobial peptide BMAP-27: the role of leucine as well as phenylalanine zipper sequences in determining its toxicity. *Biochemistry* 48, 10905-17.

(Bell and Gouyon 2003) Bell, G., and Gouyon, P. H. (2003) Arming the enemy: the evolution of resistance to self-proteins. *Microbiology* 149, 1367-75.

(Brogden et al. 2003) Brogden, K. A., Ackermann, M., McCray, P. B., Jr., and Tack, B. F. (2003) Antimicrobial peptides in animals and their role in host defences. *Int J Antimicrob Agents* 22, 465-78.

(Brogden 2005) Brogden, K. A. (2005) Antimicrobial peptides: pore formers or metabolic inhibitors in bacteria? *Nat Rev Microbiol* 3, 238-50.

(Brotz et al. 1998) Brotz, H., Bierbaum, G., Leopold, K., Reynolds, P. E., and Sahl, H. G. (1998) The lantibiotic mersacidin inhibits peptidoglycan synthesis by targeting lipid II. *Antimicrob Agents Chemother* 42, 154-60.

(Clinical and Laboratory Standards Institute 2006) Clinical and Laboratory Standards Institute. (2006) Performance standards for antimicrobial susceptibility testing; sixteenth informational supplement. CLSI document M100-S16CLSI, Wayne, Pa.

(Conlon et al. 2003) Conlon, J. M., Sonnevend, A., Patel, M., Camasamudram, V., Nowotny, N., Zilahi, E., Iwamuro, S., Nielsen, P. F., and Pal, T. (2003) A melittin-related peptide from the skin of the Japanese frog, Rana tagoi, with antimicrobial and cytolytic properties. *Biochemical and Biophysical Research Communications* 306, 496-500.

(Dathe 1997) Dathe, M., Wieprecht, T., Nikolenko, H., Handel, L., Maloy, W. L., MacDonald, D. L., Beyermann, M., and Bienert, M. (1997) Hydrophobicity, hydrophobic moment and angle subtended by charged residues modulate antibacterial and haemolytic activity of amphipathic helical peptides. *FEBS Lett* 403, 208-12.

(Diamond 2001) Diamond, G. (2001) Natures antibiotics: the potential of antimicrobial peptides as new drugs. *Biologist (London)* 48, 209-12.

(European Committee for Antimicrobial Susceptibility Testing of the European Society of Clinical Microbiology and Infectious Diseases 2003) European Committee for Antimicrobial Susceptibility Testing of the European Society of Clinical, M., and Infectious, D. (2003) Determination of minimum inhibitory concentrations (MICS) of antibacterial agents by broth dilution. *Clinical Microbiology and Infection* 9, ix-xv.

(Gautier et al. 2008) Gautier, R., Douguet, D., Antonny, B., and Drin, G. (2008) HELIQUEST: a web server to screen sequences with specific alpha-helical properties. *Bioinformatics* 24, 2101-2.

(Gennaro and Zanetti 2000) Gennaro, R., and Zanetti, M. (2000) Structural features and biological activities of the cathelicidin-derived antimicrobial peptides. *Biopolymers* 55, 31-49.

(Ginsburg and Koren 2008) Ginsburg, I., and Koren, E. (2008) Are cationic antimicrobial peptides also 'double-edged swords'? *Expert Rev Anti Infect Ther* 6, 453-62.

(Giuliani et al. 2007) Giuliani, A., Pirri, G., and Nicoletto, S. (2007) Antimicrobial peptides: an overview of a promising class of therapeutics. *Central European Journal of Biology* 2, 1-33.

(Gordon et al. 2005) Gordon Yj Fau-Romanowski, E. G., Romanowski Eg Fau-McDermott, A. M., and McDermott, A. M. (2005) A review of antimicrobial peptides and their therapeutic potential as anti-infective drugs. *Curr Eye Res* 30, 505-515.

(Hilpert et al. 2010) Hilpert, K., McLeod, B., Yu, J., Elliott, M. R., Rautenbach, M., Ruden, S., Burck, J., Muhle-Goll, C., Ulrich, A. S., Keller, S., and Hancock, R. E. (2010) Short cationic antimicrobial peptides interact with ATP. *Antimicrob Agents Chemother* 54, 4480-3.

(Jin et al. 2005) Jin, Y., Hammer, J., Pate, M., Zhang, Y., Zhu, F., Zmuda, E., and Blazyk, J. (2005) Antimicrobial activities and structures of two linear cationic peptide families with various amphipathic beta-sheet and alpha-helical potentials. *Antimicrob Agents Chemother* 49, 4957-64.

(Kaur et al. 2007) Kaur, H., Garg, A., and Raghava, G. P. (2007) PEPstr: a de novo method for tertiary structure prediction of small bioactive peptides. *Protein Pept Lett* 14, 626-31.

(Lehrer and Ganz 2002) Lehrer, R. I., and Ganz, T. (2002) Defensins of vertebrate animals. *Curr Opin Immunol* 14, 96-102.

(Lottspeich and Engels 2006) Lottspeich, F., Engels, J. W. (Hrsg.) (2006) Bioanalytik. Spektrum Akademischer Verlag.

(Marr et al. 2006) Marr, A. K., Gooderham, W. J., and Hancock, R. E. W. (2006) Antibacterial peptides for therapeutic use: obstacles and realistic outlook. *Current Opinion in Pharmacology* 6, 468-472.

(Maupetit et al. 2009) Maupetit, J., Derreumaux, P., and Tufféry, P. (2009) PEP-FOLD: an online resource for de novo peptide structure prediction. *Nucleic Acids Res* 37, W498-503.

(Maupetit et al. 2010) Maupetit, J., Derreumaux, P., and Tufféry, P. (2010) A fast method for large-scale de novo peptide and miniprotein structure prediction. *J Comput Chem* 31, 726-38.

(Ong et al. 2013) Ong, Z. Y., Gao, S. J., and Yang, Y. Y. (2013) Short Synthetic β-Sheet Forming Peptide Amphiphiles as Broad Spectrum Antimicrobials with Antibiofilm and Endotoxin Neutralizing Capabilities. *Advanced Functional Materials* 23, 3682-3692.

(Otvos et al. 2000) Otvos, L., Jr., O, I., Rogers, M. E., Consolvo, P. J., Condie, B. A., Lovas, S., Bulet, P., and Blaszczyk-Thurin, M. (2000) Interaction between heat shock proteins and antimicrobial peptides. *Biochemistry* 39, 14150-9.

(Oyston et al. 2009) Oyston, P. C., Fox, M. A., Richards, S. J., and Clark, G. C. (2009) Novel peptide therapeutics for treatment of infections. *J Med Microbiol* 58, 977-87.

(Pettersen et al. 2004) Pettersen, E. F., Goddard, T. D., Huang, C. C., Couch, G. S., Greenblatt, D. M., Meng, E. C., and Ferrin, T. E. (2004) UCSF Chimera—A visualization system for exploratory research and analysis. Journal of Computational Chemistry 25, 1605-1612

(Rausch et al. 2005) Rausch, J. M., Marks, J. R., and Wimley, W. C. (2005) Rational combinatorial design of pore-forming beta-sheet peptides. *Proc Natl Acad Sci USA* 102, 10511-5.

(Rausch et al. 2007) Rausch, J. M., Marks, J. R., Rathinakumar, R., and Wimley, W. C. (2007) Beta-sheet pore-forming peptides selected from a rational combinatorial library: mechanism of pore formation in lipid vesicles and activity in biological membranes. *Biochemistry* 46, 12124-39.

(Richter 2003) Richter, G. (2003) Praktische Biochemie. Georg Thieme Verlag.

(Shai 1999) Shai, Y. (1999) Mechanism of the binding, insertion and destabilization of phospholipid bilayer membranes by alpha-helical antimicrobial and cell non-selective membrane-lytic peptides. *Biochim Biophys Acta* 1462, 55-70.

(Stryer 1999) Stryer, L. (1999) Biochemie. Spektrum Akademischer Verlag Heidelberg.

(Subbalakshmi and Sitaram 1998) Subbalakshmi, C., and Sitaram, N. (1998) Mechanism of antimicrobial action of indolicidin. *FEMS Microbiol Lett* 160, 91-6.

(Thévenet et al. 2012) Thévenet, P., Shen, Y., Maupetit, J., Guyon, F., Derreumaux, P., and Tufféry, P. (2012) PEP-FOLD: an updated de novo structure prediction server for both linear and disulfide bonded cyclic peptides. *Nucleic Acids Res* 40, W288-93.

(Thompson et al. 1994) Thompson, J. D., Higgins, D. G., Gibson, T. J. (1994) CLUSTAL W: improving the sensitivity of progressive multiple sequence alignment through sequence weighting, position-specific gap penalties and weight matrix choice. *Nucleic Acid Research* 22, 4673-4680

(Tossi et al. 2000) Tossi, A., Sandri, L., and Giangaspero, A. (2000) Amphipathic, alpha-helical antimicrobial peptides. *Biopolymers* 55, 4-30.

(Wiegand et al. 2008) Wiegand, I., Hilpert, K., and Hancock, R. E. (2008) Agar and broth dilution methods to determine the minimal inhibitory concentration (MIC) of antimicrobial substances. *Nat Protoc* 3, 163-75.

(Wiradharma 2013) Wiradharma, N., Sng, M. Y. S., Khan, M., Ong, Z. Y., and Yang, Y. Y. (2013) Rationally Designed alpha-Helical Broad-Spectrum Antimicrobial Peptides with Idealized Facial Amphiphilicity. *Macromolecular Rapid Communications* 34, 74-80.

(Zaiou 2007) Zaiou, M. (2007) Multifunctional antimicrobial peptides: therapeutic targets in several human diseases. *J Mol Med (Berl)* 85, 317-29.

The invention claimed is:

1. A peptide consisting of an amino-terminal region A, a carboxy-terminal region C and, in between, a region B, the peptide having the general formula $$A_xB_yC_z,$$

with $3 \leq x \leq 7$, $3 \leq z \leq 7$ and $5 \leq y \leq 10$,
wherein the amino acids of A and C, independently of one another, are exclusively selected from the group consisting of Lys, Arg and combinations thereof and wherein the amino acids of B are exclusively selected from the group consisting of Val, Ile and combinations of at least two of Val, Leu, and Ile, and wherein the peptide on the C-terminus is formed as carboxamide.

2. The peptide according to claim 1, with $x+y+z \leq 20$.

3. The peptide according to claim 1, wherein the peptide is formed at least partially as beta strand in an aqueous medium.

4. The peptide according to claim 3, wherein at least 50%, 65%, 75% or 80% of the amino acids of the peptide are comprised in a single beta strand.

5. The peptide according to claim 4, wherein the peptide has no alpha-helix in an aqueous medium.

6. The peptide according to claim 1, wherein the peptide is selected from the group consisting of SEQ ID NO: 1 to SEQ ID NO: 3, SEQ ID NO: 6, SEQ ID NO: 7, SEQ ID NO: 10, SEQ ID NO: 13, SEQ ID NO: 15, SEQ ID NO: 16, SEQ ID NO: 19, SEQ ID NO: 20, SEQ ID NO: 27, SEQ ID NO: 28, SEQ ID NO: 37, SEQ ID NO. 43, and SEQ ID NO: 49.

7. The peptide according to claim 1 for use as medicament.

8. A conjugate comprising the peptide according to claim 1 and at least one further component to which the peptide is covalently and/or adsorptively bonded.

9. An antimicrobial composition comprising the peptide according to claim 1.

10. A method of treating a bacterial infection comprising administering to a subject a therapeutically effective amount of a peptide consisting of an amino-terminal region A, a carboxy-terminal region C and, in between, a region B, the peptide having the general formula $$A_xB_yC_z,$$

with $3 \leq x \leq 7$, $3 \leq z \leq 7$ and $5 \leq y \leq 10$,
wherein the amino acids of A and C, independently of one another, are exclusively selected from the group consisting of Lys, Arg and combinations thereof and
wherein the amino acids of B are exclusively selected from the group consisting of Val, Ile and combinations of at least two of Val, Leu, and Ile, and
wherein the peptide on the C-terminus is formed as carboxamide.

* * * * *